(12) United States Patent
Liang

(10) Patent No.: US 8,858,541 B2
(45) Date of Patent: Oct. 14, 2014

(54) METHODS AND DEVICES FOR REFRACTIVE TREATMENTS OF PRESBYOPIA

(71) Applicant: Junzhong Liang, Fremont, CA (US)

(72) Inventor: Junzhong Liang, Fremont, CA (US)

( * ) Notice: Subject to any disclaimer, the term of this patent is extended or adjusted under 35 U.S.C. 154(b) by 0 days.

(21) Appl. No.: 13/961,753

(22) Filed: Aug. 7, 2013

(65) Prior Publication Data
US 2013/0324983 A1  Dec. 5, 2013

Related U.S. Application Data

(62) Division of application No. 12/739,742, filed as application No. PCT/US2008/081421 on Oct. 28, 2008, now Pat. No. 8,529,559.

(60) Provisional application No. 61/000,643, filed on Oct. 29, 2007.

(51) Int. Cl.
| | |
|---|---|
| *G02C 7/02* | (2006.01) |
| *G02C 7/04* | (2006.01) |
| *A61B 3/00* | (2006.01) |
| *A61B 19/00* | (2006.01) |
| *A61F 9/008* | (2006.01) |

(52) U.S. Cl.
CPC ............. *A61F 9/00808* (2013.01); *A61F 9/008* (2013.01); *G02C 7/042* (2013.01); *A61F 2009/00895* (2013.01); *A61F 2009/0088* (2013.01); *G02C 7/044* (2013.01); *A61F 9/00819* (2013.01); *G02C 2202/22* (2013.01); *A61F 9/00812* (2013.01); *A61F 2009/00872* (2013.01)
USPC ................ 606/5; 351/159; 351/200; 128/898

(58) Field of Classification Search
USPC ............. 351/200, 246–247, 205, 219, 160 R, 351/159, 206, 208, 212, 221; 606/4, 5, 6, 606/10–15; 128/898; 623/6.11–6.24, 623/6.27–6.56, 6, 61
See application file for complete search history.

(56) References Cited

U.S. PATENT DOCUMENTS

| 6,082,856 A | 7/2000 | Dunn et al. |
|---|---|---|
| 7,261,412 B2 | 8/2007 | Somani et al. |
| 2003/0199858 A1 | 10/2003 | Schelonka |

(Continued)

FOREIGN PATENT DOCUMENTS

| JP | 2002515132 A | 5/2002 |
|---|---|---|
| JP | 2003514597 A | 4/2003 |

(Continued)

OTHER PUBLICATIONS

Office Action dated Feb. 20, 2013 for Mexican Application No. MX/a/2010/0044492.

(Continued)

*Primary Examiner* — Dawayne A Pinkney
(74) *Attorney, Agent, or Firm* — The Mueller Law Office, P.C.

(57) ABSTRACT

Presbyopia in a patient's eye is treated by inducing spherical aberration in the central section of the pupil, while the peripheral section of the pupil is treated in a manner other than the central section of the pupil. For example, the peripheral section of the pupil may remain untreated, or high-order aberration may be controlled, and/or a second area of spherical aberration may be provided with different focus power.

14 Claims, 26 Drawing Sheets

(56) References Cited

U.S. PATENT DOCUMENTS

| | | |
|---|---|---|
| 2004/0233382 A1 | 11/2004 | Lindacher et al. |
| 2005/0041203 A1 | 2/2005 | Lindacher et al. |
| 2005/0041206 A1 | 2/2005 | Vogelsang et al. |
| 2005/0088615 A1 | 4/2005 | Roffman et al. |
| 2005/0099595 A1 | 5/2005 | Lindacher |
| 2005/0143812 A1 | 6/2005 | Paul et al. |
| 2005/0246015 A1 | 11/2005 | Miller |
| 2006/0238702 A1 | 10/2006 | Glick et al. |
| 2007/0002274 A1 | 1/2007 | Somani et al. |
| 2008/0015461 A1* | 1/2008 | Somani et al. ............... 600/558 |

FOREIGN PATENT DOCUMENTS

| | | |
|---|---|---|
| JP | 2003531708 A | 10/2003 |
| JP | 2006506203 A | 2/2006 |
| JP | 2007503011 A | 2/2007 |
| JP | 2007516019 A | 6/2007 |
| WO | 0184216 A1 | 11/2001 |
| WO | 2007005261 A2 | 1/2007 |
| WO | 2009123700 | 10/2009 |

OTHER PUBLICATIONS

Office Action dated Mar. 12, 2013 for Japanese application JP 2010-531325.

Extended European Search Report dated Jul. 9, 2013 for European Patent Application 08844582.0.

Japanese office action dated Nov. 26, 2013 for JP Application No. 2010-531325.

* cited by examiner

METHODS AND DEVICES FOR REFRACTIVE TREATMENTS OF PRESBYOPIA

CROSS-REFERENCES TO RELATED INVENTIONS

This application is a divisional of U.S. application Ser. No. 12/739,742, titled "Methods And Devices for Refractive Treatments of Presbyopia", filed on Apr. 25, 2010; which claims priority to International Application No. PCT/US2008/081421, titled "Methods and Devices for Refractive Treatments of Presbyopia," which was filed on Oct. 28, 2008 by Junzhong Liang, which claims the benefit of U.S. Provisional Application No. 61/000,643 titled "Methods and Devices for Treatments of Presbyopia," which was filed on Oct. 29, 2007 by Junzhong Liang. The disclosures of these related applications are incorporated herein by reference.

FIELD OF THE INVENTION

This application relates to refractive correction of human eyes, in particular, for refractive treatments of presbyopia.

BACKGROUND OF THE INVENTION

Presbyopia is an age-related problem with near vision, due to progressive reduction in the eye's ability to focus, with consequent difficulty in reading at the normal distance. An effective refractive correction of presbyopia must provide simultaneous focus for far, intermediate, and near vision in all conditions of pupil sizes.

Diffractive intraocular lenses (IOLs) such as those described in U.S. Pat. No. 5,116,111 by Michael Simpson and John Futhey and in US 2006/0116764A1 by Michael Simpson can provide simultaneous bi-focus (far vision and near vision) correction for presbyopia, but have two inherent disadvantages: degraded night vision with night glare caused by light scattering at the junctions of diffractive zones in the lens surface, and a blind spot at intermediate distance between the far and near focus points.

Multifocal designs by controlling light distribution for far, intermediate, and near vision across different aperture size of a lens were proposed by Valdmar Portney in U.S. Pat. Nos. 5,225,858 and 6,557,998B2. These lens designs can perform better for intermediate vision than Simpson's diffractive IOLs, but are also known to be inferior for performance at near vision. Moreover, Portney's lenses fail to achieve their full potential as they are based on simple geometric ray tracing, without taking into account the diffraction effect of light propagation.

Aspheric lenses were also proposed in U.S. Pat. No. 6,923,539B2 by Michael Simpson and in U.S. Pat. Nos. 5,166,711 and 6,409,340B1 by Valdmar Portney. These lenses have a periodic refractive power distribution across a lens. While Simpson's lens can increase focus depth for a mono-focal lens as illustrated in FIG. 9 of U.S. Pat. No. 6,923,539B2, such lens is typically not suitable for presbyopic correction.

Spherical aberration across the pupil of an eye produces different focusing power at different pupil radii. Negative spherical aberration across pupil of an eye was proposed for mitigation of presbyopia by Seema Somani and Kingman Yee in U.S. Pat. No. 7,261,412 B2. There, the inventors noticed that negative spherical aberration across the entire pupil can shift the center of the focus range from far to an intermediate distance because negative spherical aberration produces focus power for far vision at the pupil center to intermediate vision at the pupil periphery.

However, inducing spherical aberration across an entire pupil of an eye has at least two limitations for presbyopic corrections. First, the total amount of spherical aberration induced across the pupil cannot be too strong to cause nighttime symptoms such as glare, halo and starburst, which is one of the fundamental reasons why lenses with significant spherical aberration has not been used in multifocal IOLs and contact lenses for presbyopic treatments. Second, Somani and Yee's method in U.S. Pat. No. 7,261,412 B2 is typically not sufficient for presbyopic treatments because the small amount of spherical aberration across the entire pupil only shifts the center of focus range and does not increase focus depth. Still further, currently known methods of spherical aberration for presbyopic corrections have failed to address issues of induced nighttime symptoms (glare, halo, starburst) and increase focus depth of an eye for far vision, intermediate vision and near vision, thus rendering such solutions less than desirable.

Consequently, although many configurations and methods for vision correction for treatment of presbyopia are known in the art, all or almost all of them suffer from one or more disadvantages. Thus, there is still a need to provide improved configurations and methods for vision correction for treatment of presbyopia.

SUMMARY OF THE INVENTION

The present invention is directed to devices and methods for correcting presbyopia in which optical properties in the pupil of an eye are changed such that a central section of the pupil is differently treated than a peripheral section, and wherein treatment of the central section includes induction of spherical aberration in the central section of the pupil.

In one aspect of the inventive subject matter, a method of treating presbyopia of a patient's eye (wherein the eye has a natural pupil that comprises a central pupil section at equal or less than 4 mm in diameter and a surrounding periphery pupil section for receiving light at low-light conditions) includes a step of inducing spherical aberration in the central pupil section, and another step of preserving or reducing high-order aberrations in the periphery pupil section that are present prior to treatment.

Particularly contemplated methods may further comprise a step of attenuating or blocking passage of light into the eye via the periphery pupil section. In most cases, the induced spherical aberration in the central pupil section is a positive spherical aberration or a negative spherical aberration, and where desired, the induced spherical aberration in the central pupil section comprises a positive spherical aberration in a first zone and a negative spherical aberration in a second zone. Thus, the central pupil section may be divided into two concentric optical sections having spherical aberrations of opposite signs. It is still further preferred that the induced spherical aberration in the central pupil section is custom designed and based on the pupil size of an eye under at least one luminance condition. Contemplated methods will further include a step of reducing or eliminating at least one of a focus error and astigmatism in the eye, and/or a step of reducing or eliminating 3rd order Zernike aberrations in the eye. In some aspects, contemplated methods may be implemented in a laser vision correction in which a processor generates an ablation pattern of laser energy for ablation of a corneal tissue of the eye, wherein the ablation pattern is based at least in part on a determined refraction profile across the pupil, and wherein laser energy is directed onto the corneal tissue of the eye to achieve the generated ablation pattern.

Consequently, a multifocal and refractive corrective ophthalmic lens is contemplated in which the lens is configured to provide a baseline diopter power extending across the lens in an amount effective to correct a far vision defect, and wherein the lens is further configured to have a spherical aberration in a central section of the lens in an amount effective to increase focus depth of an eye, and wherein the lens is still further configured as implantable lens or wearable lens.

In another aspect of the inventive subject matter, a method of treating presbyopia of a patient's eye (wherein the eye has a natural pupil that comprises a central pupil section at equal or less than 4 mm in diameter and a surrounding periphery pupil section for receiving light at low-light conditions) will include a step of producing a first set of focus power and spherical aberration in the central pupil section and a second set of focus power and spherical aberration in the periphery pupil section, wherein first and second sets are distinct.

Most preferably, the spherical aberration in the central pupil section is selected to increase focus depth of the eye for a pupil size of equal or less than 4 mm in diameter, and wherein the focus power and spherical aberration in the pupil periphery pupil section are selected to improve image quality for far vision at the low-light conditions, and/or the induced spherical aberration in the central pupil section is custom determined based on the pupil size of an eye under at least one luminance condition.

Where desired, it is contemplated that such methods further include a step of configuring at least one of the first and second sets to reduce or eliminate at least one of a focus error and astigmatism in the eye, and/or a step of configuring at least one of the first and second sets to reduce or eliminate 3rd order Zernike aberrations in the eye. As above, contemplated methods may be implemented in a laser vision correction in which a processor generates an ablation pattern of laser energy for ablation of a corneal tissue of the eye, wherein the ablation pattern is based at least in part on a determined refraction profile across the pupil, and wherein laser energy is directed onto the corneal tissue of the eye to achieve the generated ablation pattern.

Consequently, a multifocal and refractive corrective ophthalmic lens is contemplated in which the lens has a plurality of concentric optical sections, wherein at least two of the optical sections have distinct sets of focus power and spherical aberration, and wherein the lens is configured as implantable lens or wearable lens.

Various objects, features, aspects and advantages of the present invention will become more apparent from the following detailed description of preferred embodiments of the invention.

BRIEF DESCRIPTION OF THE DRAWING

FIG. 8c shows another embodiment that has a clear optical section replacing the annular opaque mask 83 in FIG. 8a.

DETAILED DESCRIPTION OF THE INVENTION

Figure 1:
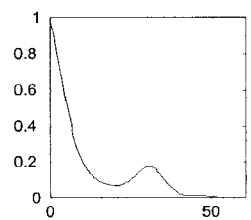
FIG. 1 shows the calculated MTFs (modulation transfer function) and retinal images of an eye for far vision, intermediate vision and near vision with a refractive element that restricts effective pupil of an eye and induces high-order aberration (spherical aberration) in central pupil in accordance to a present invention. The eye is assumed to have no ability of accommodation.
Figure 1:
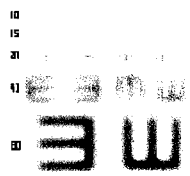
Figure 1:
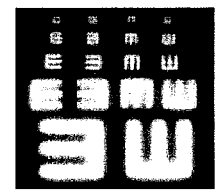
Figure 1:
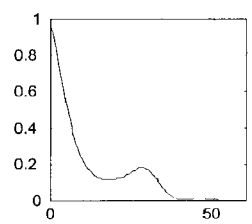
Figure 1:
Figure 1:
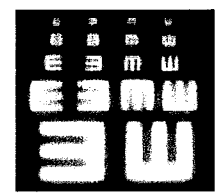
Figure 1:
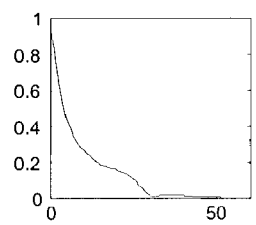
Figure 1:
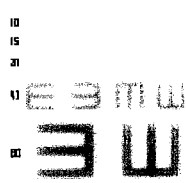
Figure 1:
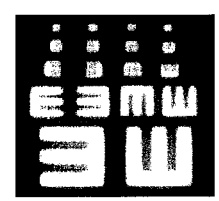
Figure 1:
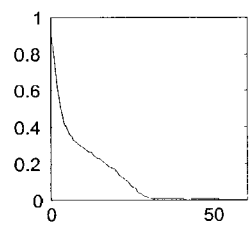
Figure 1:
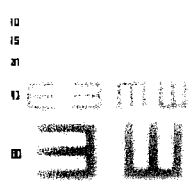
Figure 1:
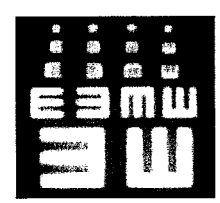
Figure 1:
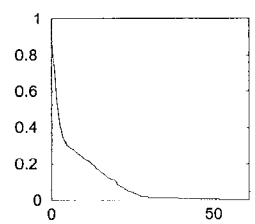
Figure 1:
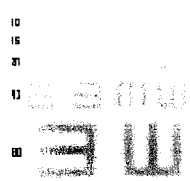
Figure 1:
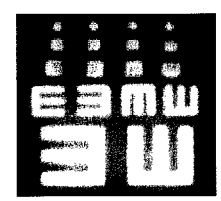

Improving Depth of Focus for the Treatments of Presbyopia by Restricting Pupil Size and Inducing Spherical Aberration within a Small Pupil of an Eye Optical property of an eye with a refractive element can generally be described by a complex pupil function P(r) such as $$P(r)=A(r)*\exp(i2\pi\Phi(r)/\lambda)*S(r)*\exp(i2\pi W(r)/\lambda), \quad (1)$$

where r is the polar radius across pupil of an eye. A (r) and Φ(r) represent the amplitude transmittance function and the wavefront distribution of a refractive element, respectively. S (r) and W(r) are the amplitude transmittance function (Stiles-Crawford effect) and wavefront errors across pupil of an individual eye, respectively. We only include the radial component of the pupil function across pupil for simplicity.

We describe a method of increasing depth of focus for an eye by reducing effective pupil size of an eye for photopic vision and inducing spherical aberration in the central pupil area. Reducing (restricting) pupil size of an eye can be expressed by an amplitude transmittance function A (r) in Eq. 1 as $$A(r)=\text{circ}(r/r_0) \quad (2)$$

where $r_0$ is the radius of the reduced pupil, and circ($r/r_0$) is a circular function, which equals to 1 if r is equal to or less than $r_0$ and equals to zero if r is larger than $r_0$. If the aperture size 2 $r_0$ is smaller than a natural pupil of an eye in photopic conditions, the aperture of the refractive element actually determines the effective pupil size of an eye. Inducing spherical aberration within the restricted pupil area can be expressed by $$\Phi(r)=c1*(r/r_0)^4 \quad (3)$$

The coefficient c1 measures the amount of spherical aberration across the pupil within the restricted aperture.

Of course, an optical element for refractive correction often includes a conventional sphero-cylindrical correction as well. Conventional sphero-cylindrical corrections are not included in our description for simplicity. However, corrections for presbyopia may include a focus offset in order to set the focal point away from the far point of an eye. Combining the focus offset and the induced spherical aberration we can obtain a wavefront distribution for treatments of presbyopia as $$\Phi(r)=c1*(r/r_0)^4+c2*(r/r_0)^2 \quad (4)$$

where c2 measures the focus offset.

In one example, we chose a restricted aperture of 1.6 mm ($r_0$=0.8 mm). Within such a small restricted pupil, it is reasonable to assume that the Stile-Crawford effect (S(r)) is a constant and the phase errors of an eye (W(r)) have no high order aberrations such as spherical aberration and the wavefront error of an eye is simply described by a focus error for different focusing positions, i.e., $$W(r) = c_3 * (r/r_0)^2 \quad (5)$$

while c3 measures focus error for objects at different viewing distances.

A positive spherical aberration, which causes the eye to have more refractive power at the center than at the edge, of 1.34 µm across the restricted pupil (c1=1.34 µm) can be induced within the restricted pupil, which can also be expressed as 0.1 (Z12(r)+3.87*Z4(r)) in Zernike polynomials. Z12 and Z4 are Zernike polynomials in the form of $Z12(r)=2.236(6*r^4-6*r^2+1)$ and $Z4(r)=1.732(2*r^2-1)$.

The combination of a small restricted pupil and the induced spherical aberration can yield large focus depth for a presbyopia treatment. Because a positive spherical aberration will shift focus of the eye to more hyperopic, a focus offset of about 4.2D can be included to make the eye to have best image quality for far vision. Without the positive spherical aberration (c1=0), the focus offset would make the eye in focus at a near object at 24 cm.

FIG. 1 shows the calculated MTF (Modulation Transfer Function, left column) and retinal images of an eye (middle and right columns) without accommodation from an eye for far vision (at infinity: top row; 3 meter away: $2^{nd}$ row), intermediate vision (0.7 meter away: $3^{rd}$ row; 0.5 meter away: $4^{th}$ row), and near vision (0.33 meter away: bottom row). MTFs of the eye are calculated from the pupil function based equation (1), (2), (4), and (5) with the assumptions that s(r)=1. The abscissa of MTF is spatial frequency in cycles/deg. The letters of acuity chart are for an acuity of 20/10 (the smallest), 20/15, 20/20, 20/40, and 20/80 (the largest), respectively.

For the letters on the retina to be recognized by human subjects, the contrast for each letter in the retinal image has to be greater than a retinal threshold. If we make assumptions that the contrast thresholds for a normal retina is 9% for 20/20, 5% for 20/30, and 2.5% for 20/40 according to known experimental data, we can estimate acuity of the eye from the modulation-transfer function shown in the first column in FIG. 1.

FIG. 2 shows the estimated acuity for an eye with a refractive element that restricts pupil size to 1.6 mm and induces a positive spherical aberration and a focus offset of 4.2D. Three important features are seen. First, the eye has an excellent vision (20/20) for far objects with a focus depth of more than 1 Diopter, and night vision issues such as glare, halo would not be expected. Second, the eye has acceptable near and intermediate vision with an estimated acuity of 20/30 from 1 meter to 0.33 meters. It is possible that the eye has an acuity of 20/40 up to 0.2 meters in front of an eye.

In another example, we chose a restricted aperture of 1.6 mm ($r_0$=0.8 mm), and a negative spherical aberration, which causes the eye to have more refractive power at the edge than at the center, of 1.34 µm across the restricted pupil (c1=−1.34 µm), and a focus offset of about −1.2 Dioptors that reduces refractive power of the eye's optics. FIG. 2b shows the estimated acuity for an eye with such a refractive correction. Two important features are seen. First, the eye has an excellent near vision acuity (20/20) for near object. Second, a focus offset of about −1.2 D will make the eye 20/30 or better from far vision to intermediate distant vision.

Figure 2A:
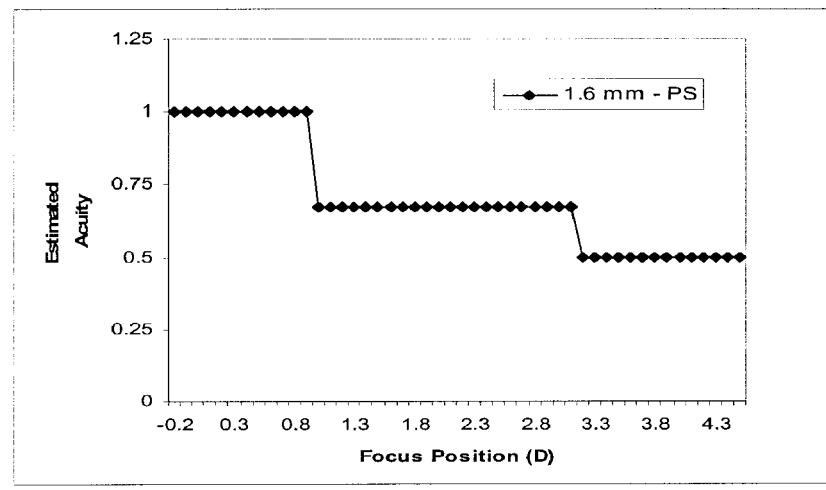
FIG. 2a shows the estimated acuity for an eye with a refractive element that restricts pupil size of an eye to 1.6 mm and induces a positive spherical aberration in central pupil area, and a focus offset of 4.2D.
Figure 2B:
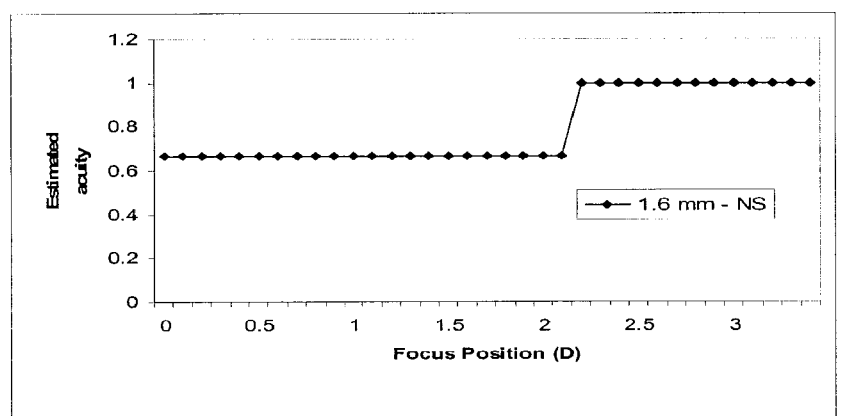
FIG. 2b shows estimated acuity for an eye with a refractive element that restricts pupil size of an eye to 1.6 mm and induces a negative spherical aberration in central pupil area.

Looking into FIG. 2a and FIG. 2b, one can easily realize a method for obtaining exceptional binocular vision for near and far objects by having one eye corrected with a positive spherical aberration and the other eye with a negative spherical aberration. It must be emphasized that restricting pupil size as well as applying a focus offset are necessary for both eyes.

Figure 3A:
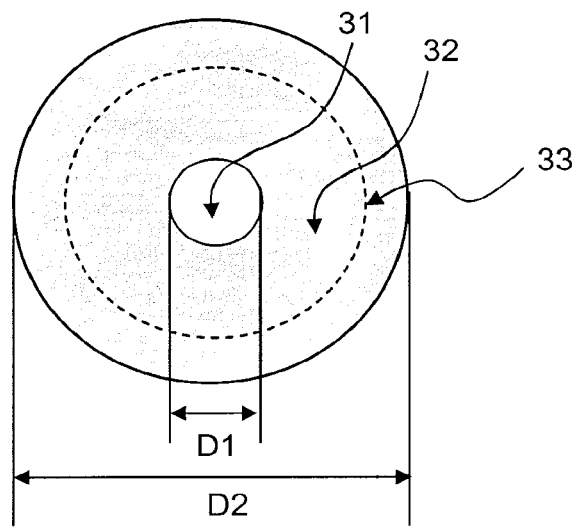
FIG. 3a shows a schematic view of an optical element to be implanted into or worn on an eye for presbyopic treatments in accordance to a present invention. The refractive element restricts pupil size of an eye for photopic vision and induces spherical aberration in the central pupil.

FIG. 3a shows an optical element to be implanted into or worn on an eye for presbyopic treatments in accordance to a present invention. The refractive element comprises a central clear optical section 31 that not only provides conventional sphero-cylindrical corrections but also induces spherical aberration within the pupil center, and an annular mask 32 that blocks or attenuates light beyond the central optical section and up to natural pupil of an eye 33 under mesopic condition (photopic conditions at very low light). The refractive element restricts pupil size of an eye for photopic vision and induces spherical aberration in the central pupil. The diameter of the central optical section D1 is between 1.4 mm and 2 mm. The outer diameter of the annular section D2 is between 3.5 mm to 6 mm, depending on the largest pupil of individual eyes at mesopic conditions (photopic condition at low light level). The optics in the central optical section may include a focus offset, depending on the induced amount of spherical aberration.

Figure 3B:
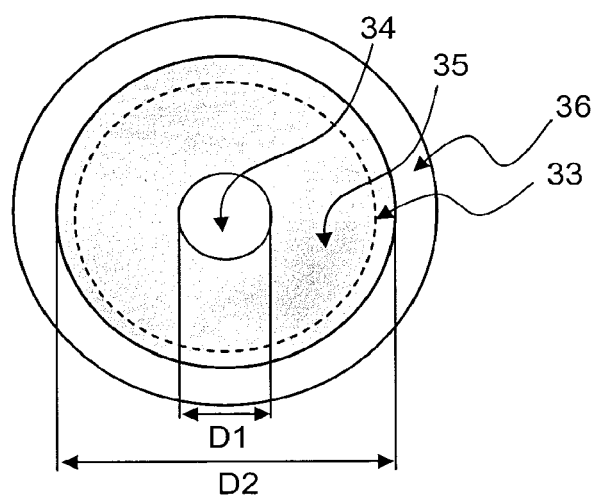
FIG. 3b shows a schematic view of an optical element to be implanted into or worn on an eye for presbyopic treatments in accordance to a present invention. The refractive element restricts pupil size of an eye for photopic vision and induces spherical aberration in the central pupil. The optical element also includes an outer transparent section for increased photon efficiency for scotopic vision (rod vision).

FIG. 3b shows an optical element to be implanted into or worn on an eye for presbyopic treatments in accordance to a present invention. The refractive element comprises a central clear optical section 34 that not only provides conventional sphero-cylindrical corrections but also induces spherical aberration within the pupil center, and an annular mask 35 that blocks or attenuates light beyond the central optical section and up to natural pupil of an eye 33 for mesopic conditions. Inducing spherical aberration can be achieved by utilizing at least one aspheric surface in the lens making. Beyond the natural pupil of the eye for mesopic vision, there is a transparent section 36 that allows the eye to collect photons for scotopic conditions (rod vision). The diameter of the central optical section D1 is between 1.4 mm and 2 mm. The outer diameter of the annular section D2 is between 3.5 mm to 6 mm, depending on the largest pupil of individual eyes at mesopic conditions (photopic condition at low light level). The optics in the central optical section may include a focus offset that depends on the induced amount of spherical aberration.

The optical element in FIG. 3a and FIG. 3b can be an intraocular lens (IOL) made with conventional process for spherical and aspheric lenses known in the prior art. At least one surfaces of the lens has to be aspheric in order to induce the desired spherical aberration. The annular opaque or partially transparent section can be obtained by coating or tinting a portion of a clear lens section, and can also be obtained by sandwiching an opaque layer into a clear lens.

Restricting pupil size and inducing spherical aberration within a small pupil of an eye can also be achieved by an IOL in combination with a corneal inlay. The IOL will provide a focus offset and certain amount of spherical aberration at the center of the lens in addition to a conventional sphero-cylindrical correction. Controlling light transmittance in an annular section can be achieved by a device like a corneal inlay implanted into the cornea.

Figure 4:
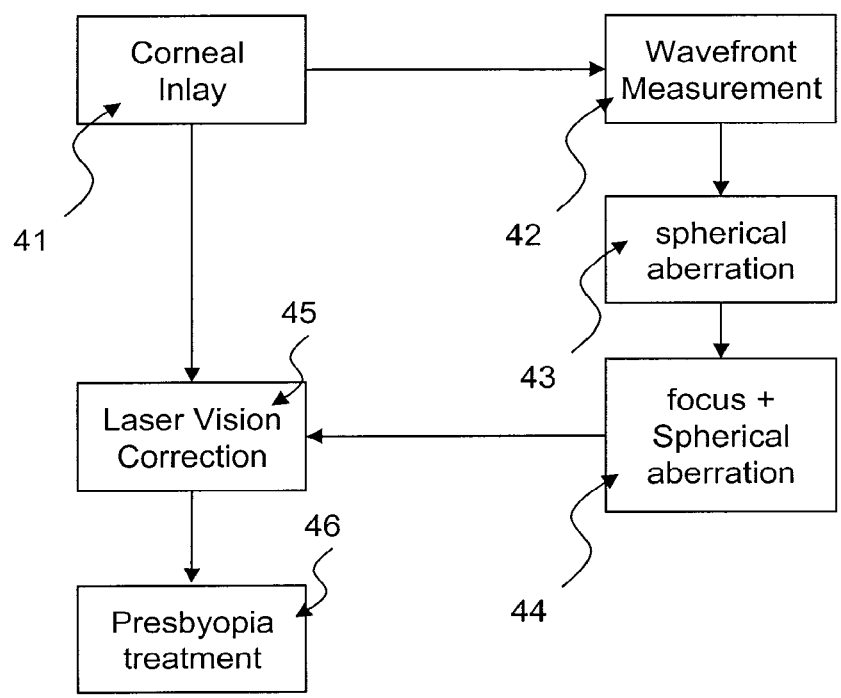
FIG. 4 shows a method for increasing focus depth of an eye with a corneal inlay in combination with a laser refractive correction in accordance to a present invention.

Restricting pupil size and inducing spherical aberration within a small pupil of an eye can also achieved by a corneal inlay in combination with a procedure like a laser vision correction. A corneal inlay can be used to block or attenuate the light in an annular zone across pupil of an eye. A laser refractive surgery can be used to produce a desired amount of spherical aberration as well as a desired focus offset to properly set the focus range of an eye. A method for such a procedure is shown in FIG. 4, comprising the steps of: 1) implant a corneal inlay into an eye 41; 2) measure wave aberration of the eye 42; 3) determine a desired focus offset 44 as well as a desired amount of spherical aberration 43 to be produced by a laser refractive surgery; 3) perform a procedure of laser refractive surgery 45 based on the determined focus error and spherical aberration. Refractive correction of conventional sphero-cylindrical corrections can also be performed in the laser procedure.

Figure 5:
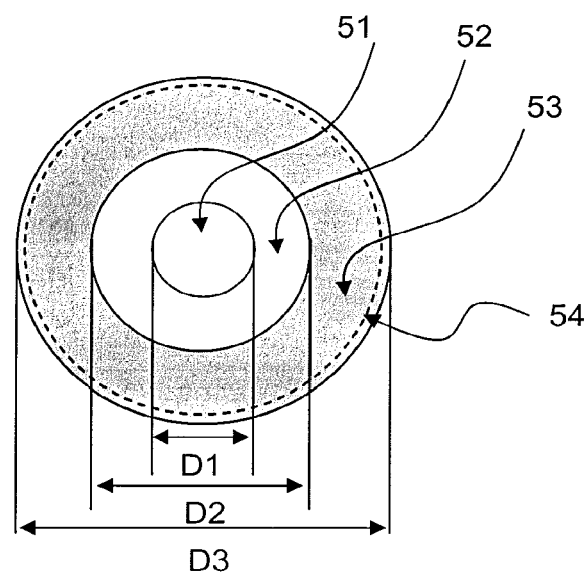
FIG. 5 shows a schematic view of a method for increasing focus depth of an eye by restricts effective pupil of an eye and inducing spherical aberration in opposite signs in two optical sections that are transparent.

Improved Focus Depth of an Eye by Inducing Spherical Aberration with Opposite Signs in a Plurality of Optical Zones Devices that reduce effective pupil of an eye to less than 2 mm can increase focus depth for treatments of presbyopia, but also reduce total light into an eye considerably. FIG. 5 shows a method that will utilize a relatively large natural pupil of an eye and increase focus depth of an eye by inducing spherical aberration with opposite signs in a plurality of optical zones. Optics of an eye under photopic conditions is divided into 3 zones: the central zone 51, the middle zone 52, and the outer zone 53. In this method of refractive correction, both 51 and 52 are clear and transparent to light wave while the outer section 53 blocks or attenuates light at pupil periphery. In addition to a conventional sphero-cylindrical correction, the clear optical sections 51 and 52 will have different focus offsets and spherical aberration with opposite signs. Natural pupil of an eye in a mesopic viewing condition is shown by 54.

In one example, the central clear section 51 has a diameter of 1.6 mm and has a positive spherical aberration about 1.34 um (or 0.1 (Z12(r)+3.87 Z4(r)) and a focus offset of 4.0 Dioptors. Outside the central clear section, the annual section 52 is transparent and has a diameter of 3 mm. Section 52 has a different focus power (0 D) and a negative spherical aberration of about 4.3 um (or −0.32 (Z12(r)+3.87 Z4(r)) at the outer edge of 52. Beyond 51 and 52 there is an annular mask section that blocks or attenuates most light beyond the central optical sections for photopic conditions. The outer diameter of the annular section is between 3.5 mm to 6 mm, depending on the largest pupil of an individual eye at mesopic conditions (photopic condition at low light level).

Figure 6:
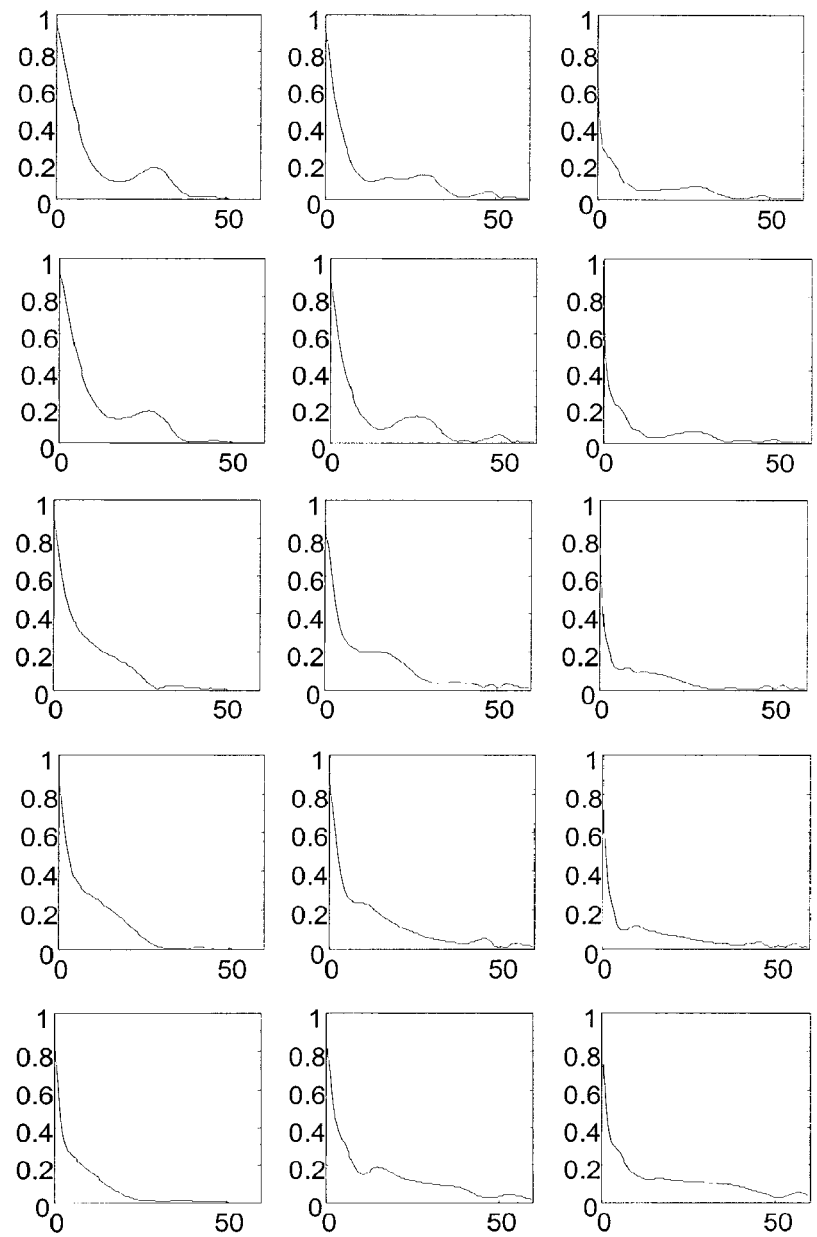
FIG. 6 shows the calculated MTFs of an eye with an optical element for increasing focus depth of an eye by restricting effective pupil of an eye in combination with inducing spherical aberration in opposite signs in two optical sections.

FIG. 6 shows the calculated MTF of an eye without accommodation for far vision (at infinity: top row; 3 meter away: $2^{nd}$ row), intermediate vision (0.7 meter away: $3^{rd}$ row; 0.5 meter away: $4^{th}$ row), and near vision (0.33 meter away: bottom row). Three pupil sizes are considered: 1.5 mm pupil on the left, 2 mm pupil in the middle, and 3 mm pupil on the right. The abscissa of MTF plots is spatial frequency in cycles/deg.

Three features can be noticed for this method of presbyopic treatments. First, the new method has identical optical quality and focus depth as that shown in FIG. 1 and FIG. 2a when the pupil of an eye is less than 1.6 mm. Second, the new method has improved image quality for near vision and intermediate vision for larger pupil, shown at the bottom three rows. Third, the new method has reduced image quality for far vision (top two rows) at night, but has improved photon efficiency with a pupil size of 3 mm instead of 1.6 mm.

Figure 7:
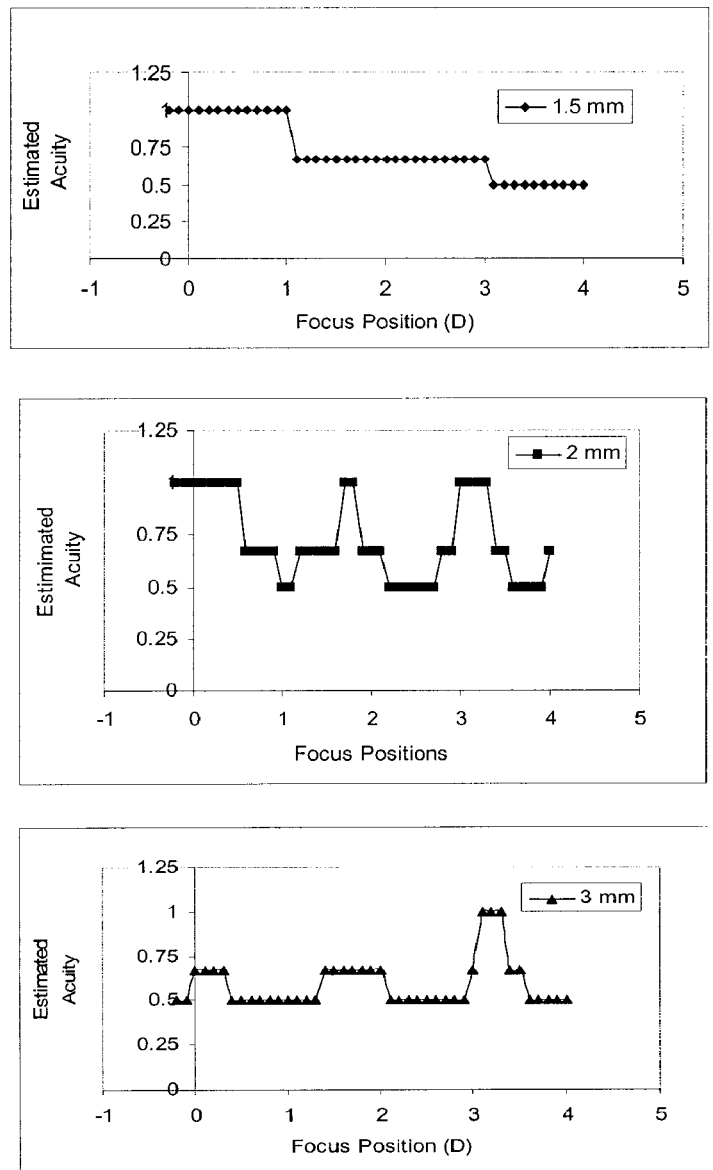
FIG. 7 shows estimated acuity based on the calculated MTFs of an eye shown in FIG. 6.

FIG. 7 shows estimated acuity based on calculated retinal contrast (MTF) of an eye like those shown in FIG. 6. We consider the same three pupil size in FIG. 6 for a range of focus distance from infinity (0 D) to near object at 0.25 meters (4 D). It is seen that the estimated acuity is 20/40 or better for all three pupil sizes and over a focus range of 4 Dioptors. For a small 1.5 mm pupil, the estimated acuity is the same as shown in FIG. 2a. For pupil sizes larger than 1.6 mm, it is also seen that there are three regions with better acuity than 20/40: far vision (<0.3D), intermediate vision (~2D), and near vision (~3D). Additionally, the method described in FIG. 5 will allow more light (about 3.5×) for night vision in comparison to the methods with a small pupil size of 1.6 mm.

Figure 8A:
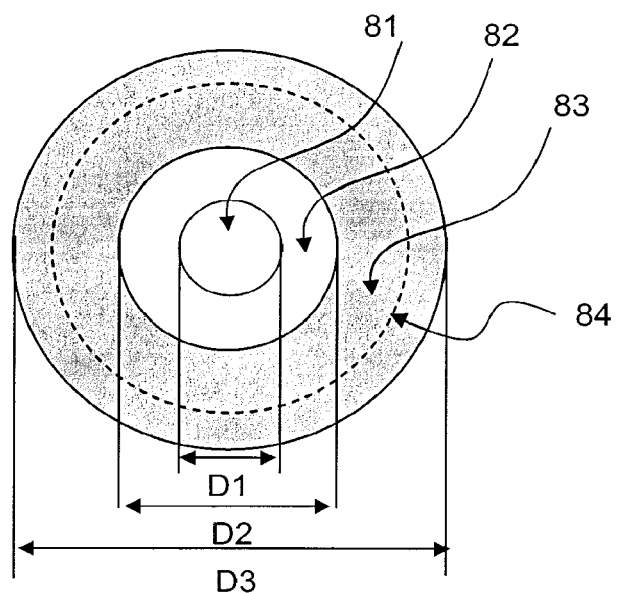
FIG. 8a shows a schematic view of an optical element to be implanted into or worn on an eye for presbyopic treatments in accordance to a present invention. The refractive element restricts pupil size of an eye for photopic vision and induces spherical aberration in opposite signs in two optical sections.

FIG. 8a shows an optical element to be implanted into or worn on an eye for presbyopic treatments in accordance to a present invention. The refractive element restricts pupil size of an eye for photopic vision and induces spherical aberration with opposite signs in two optical sections. Inducing spherical aberration can be achieved by utilizing at least one aspheric surface in the lens making. The refractive element comprises a central circular optical section 81, an annular optical section 82, and an annular mask 83 that blocks or attenuates light beyond the central optical sections and up to natural pupil of an eye 84 in mesopic conditions. The refractive element provides conventional sphero-cylindrical correction, restricts pupil size of an eye for photopic vision, and induces spherical aberration with opposite signs in two optical sections. The diameter of the central optical section D1 is between 1.4 mm and 2 mm. The outer diameter of the annular section D2 is between 2.5 mm to 3.5 mm while the outer diameter of the annular section is between 3.6 mm and 12 mm in diameter.

Figure 8B:
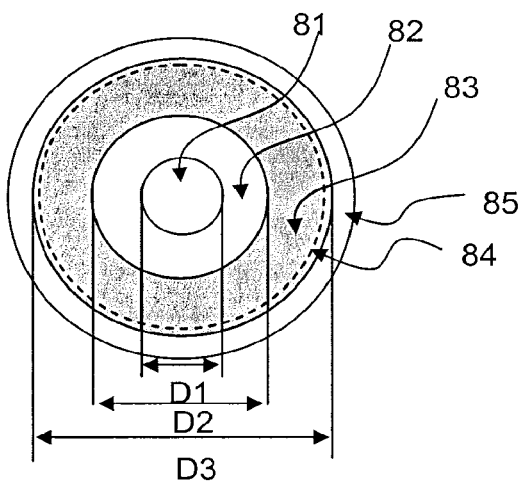
FIG. 8b shows a schematic view of another optical element to be implanted into or worn on an eye for presbyopic treatments in accordance to a present invention. The refractive element restricts pupil size of an eye for photopic vision and induces spherical aberration in opposite signs in two optical sections. The optical element also includes an outer transparent section for increasing photon efficiency for scotopic vision (rod vision).

FIG. 8b shows another optical element to be implanted into or worn on an eye for presbyopic treatments in accordance to a present invention. Differing from the device in FIG. 8a, this device has a clear optical section 85 outside the annular mask section for increased photon efficiency for scotopic vision (rod vision).

Figure 8C:
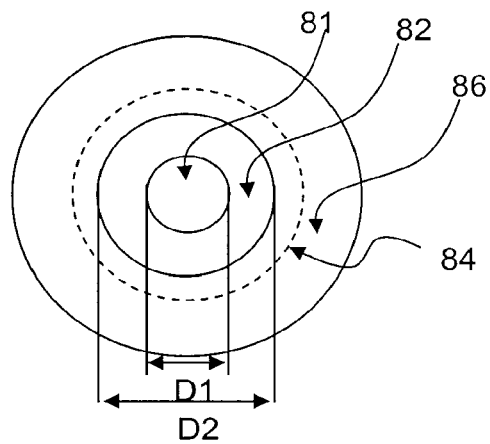

Another embodiment is shown in FIG. 8c. Differing from the device in FIG. 8a, the device has a clear optical section 86 that replaces the annular opaque mask 83. Section 86 may or may not control high-order aberrations at the pupil periphery.

The optical element in FIG. 8a, FIG. 8b and FIG. 8c can be an intraocular lens (IOL) or a contact lens made with conventional processes for spherical and aspheric lenses known in the prior art. At least one surfaces of the lens has to be aspheric in order to induce the desired spherical aberration. The annular opaque or partially transparent section can be obtained by coating or tinting a portion of a clear lens, and can also be obtained by sandwiching an opaque layer into a clear lens.

Increasing Focus Depth of an Eye by Inducing Spherical Aberration in Central Pupil and Controlling High-Order Aberration at Pupil Periphery We ignored high-order aberrations (spherical aberration) in individual eyes so far because the methods and devices described contain an annular mask that limits the effective pupil size of an eye to a relative small value that is less than or equal to 3 mm.

Normal human eyes usually have a negative spherical aberration for a large pupil just like most positive lenses. The magnitude of spherical aberration is often less than 4 μm for a 6 mm pupil (−0.3 (Z12+3.87 Z4)) in a normal population. Table 1 shows spherical aberration in normal human eyes at different pupil sizes with a spherical aberration up to 4 mm for a 6 mm pupil in three cases.

TABLE 1

Typical spherical aberration in normal human eyes

| Pupil size | 2 mm | 3 mm | 4 mm | 5 mm | 6 mm |
|---|---|---|---|---|---|
| Spherical aberration (μm) for −0.1 (Z12(r) + 3.87Z4(r)) | −0.02 | −0.08 | −0.26 | −0.65 | −1.34 |
| Spherical aberration (μm) for −0.2 (Z12(r) + 3.87Z4(r)) | −0.03 | −0.17 | −0.53 | −1.29 | −2.68 |
| Spherical aberration (μm) for −0.3 (Z12(r) + 3.87Z4(r)) | −0.05 | −0.25 | −0.79 | −1.94 | −4.02 |

It is seen that spherical aberration in a small pupil (<3 mm in diameter) for a real eye is negligible, but can be significant for a pupil larger than 4 mm in diameter. Therefore, we have to deal with high-order aberrations as well as spherical aberration in human eyes if we design treatments of presbyopia for a pupil size larger than 3 mm.

Figure 9:
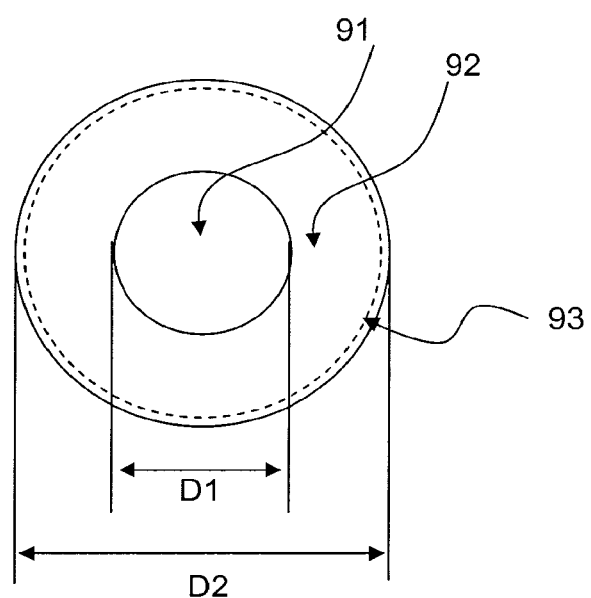
FIG. 9 shows a method for increasing focus depth of an eye by inducing spherical aberration in central pupil and controlling high-order aberration at pupil periphery.

We describe methods for increasing focus depth of an eye for presbyopia treatments by dividing a pupil of eye in a plurality of sections and controlling spherical aberration in them separately. As shown in FIG. 9, optics of an eye in photopic conditions is divided into two sections 91 (pupil center) and 92 (pupil periphery). Natural pupil is shown by 93. Increasing focus depth of an eye can be achieved by inducing spherical aberration in central pupil and controlling high-order aberration at pupil periphery at the same time. The diameter of the pupil center D1 is between 2 mm and 4 mm and the outer diameter of D2 is between 3.5 mm and 6 mm.

Figure 10:
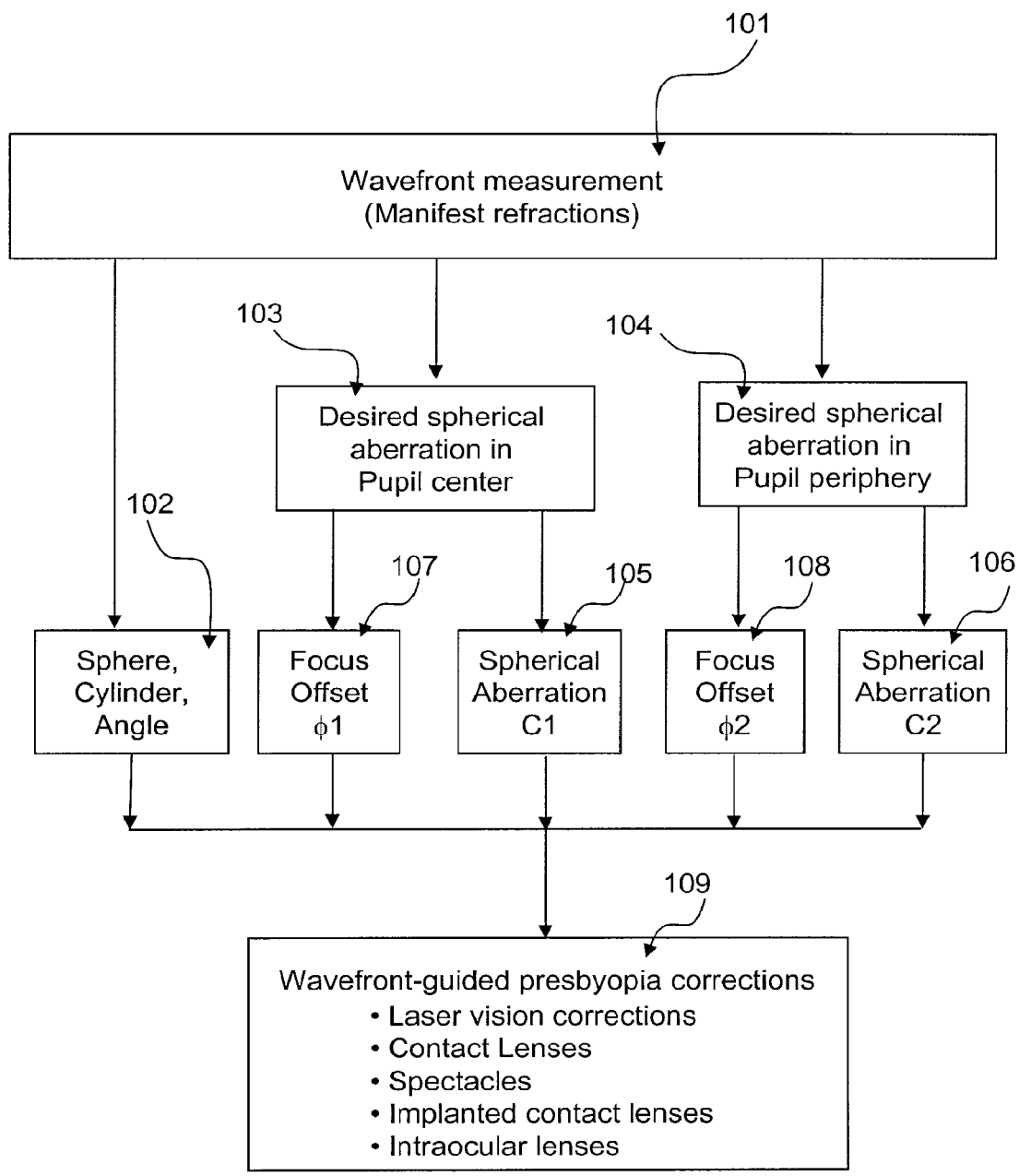
FIG. 10 shows a process for increasing focus depth of an eye by inducing spherical aberration in central pupil and controlling high-order aberration at pupil periphery.

FIG. 10 shows a process for increasing focus depth of an eye by inducing spherical aberration in central pupil and controlling high-order aberration at pupil periphery. First, wave aberration 101 is measured with a wavefront aberrometer. The wavefront aberrometer reports not only conventional sphero-cylindrical corrections but also high-order aberrations such as spherical aberration, coma and etc. Manifest refractions such as sphero-cylindrical powers as well as an accommodation range of an eye are also measured subjectively. Second, a sphero-cylindrical correction 102 for a correction element, with which the eye is made emmetropic for far vision, is determined. Third, desired magnitudes of spherical aberration are determined in at least 2 pupil sections such as in the pupil center 103 and in the pupil periphery 104. Fourth, spherical aberration in the correction element is determined for the pupil center 105 and for the pupil periphery 106 based on the eye's high-order aberrations 101 as well as the desired spherical aberration 103 and 104. Fifth, focus offsets at pupil center 107 and at pupil periphery 108 for the correction element are determined. Lastly, wavefront-guided presbyopic corrections 109 can be achieved for laser vision corrections, contact lenses, spectacles, implanted contact lenses and intraocular lenses based on three sets of refractive parameters. They included a conventional sphero-cylindrical correction across entire pupil of an eye 102, magnitudes of spherical aberration in pupil center 105 and pupil periphery 106, and focus offsets in pupil center 107 and in pupil periphery 108.

TABLE 2

Parameters of a refractive correction for presbyopia

|  | Central Pupil | Pupil Periphery |
| --- | --- | --- |
| Outer Diameter (mm) | 2.5 | 5 |
| Desired Spherical aberration $\rho^4$ (μm) | −4 | 4 |
| Focus Offset (D) | −0.6 | 1.1 |

In one embodiment, significant negative spherical aberration is induced in the pupil center while a positive spherical aberration is induced at pupil periphery. As an example, Table 2 lists the parameters for one of these corrections. First, optics of an eye is divided into two sections: the central 2.5 mm pupil and the outer pupil about 5 mm in diameter. Second, a negative spherical aberration of about −4 μm (−0.3(Z12(r)+3.87 Z4(r)) will be induced in the central pupil while a positive spherical aberration about 4 μm (0.3(Z12(r)+3.87 Z4(r)) is controlled at the outer pupil section. The focus offset for each optical size is −0.6 Dioptors and 1.1 Dioptors, respectively.

Figure 11:
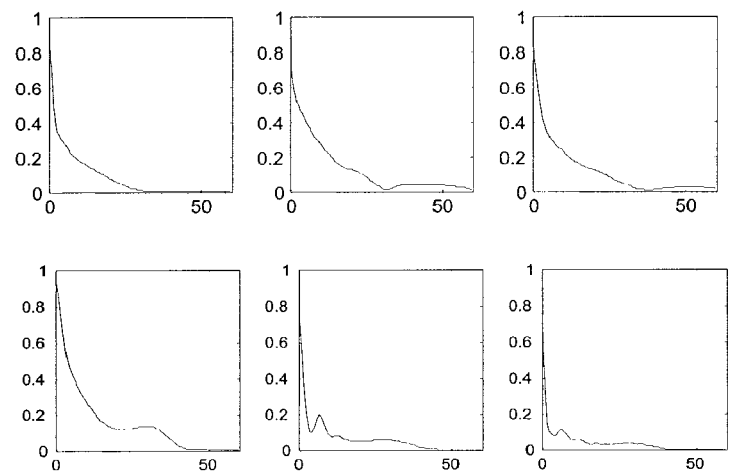
FIG. 11a shows MTFs of an eye for a far object and for a near object in one example for increasing focus depth of an eye by inducing spherical aberration in central pupil and controlling high-order aberrations at pupil periphery.
FIG. 11b shows calculated retinal images of acuity charts on a retina of an eye for a far vision and for near vision in one example for increasing focus depth of an eye by inducing spherical aberration in central pupil and controlling high-order aberrations at pupil periphery.
Figure 11B:
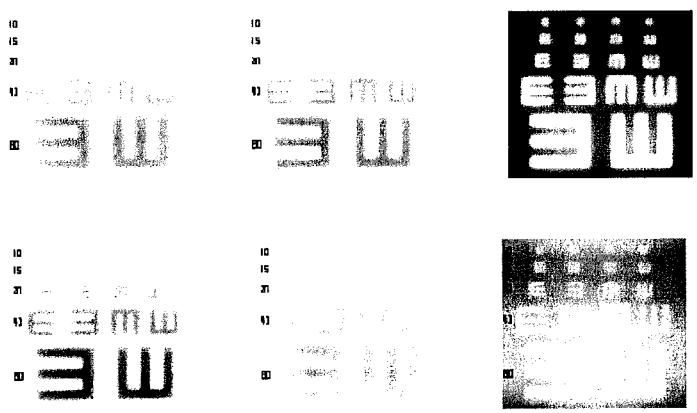
Figure 12:
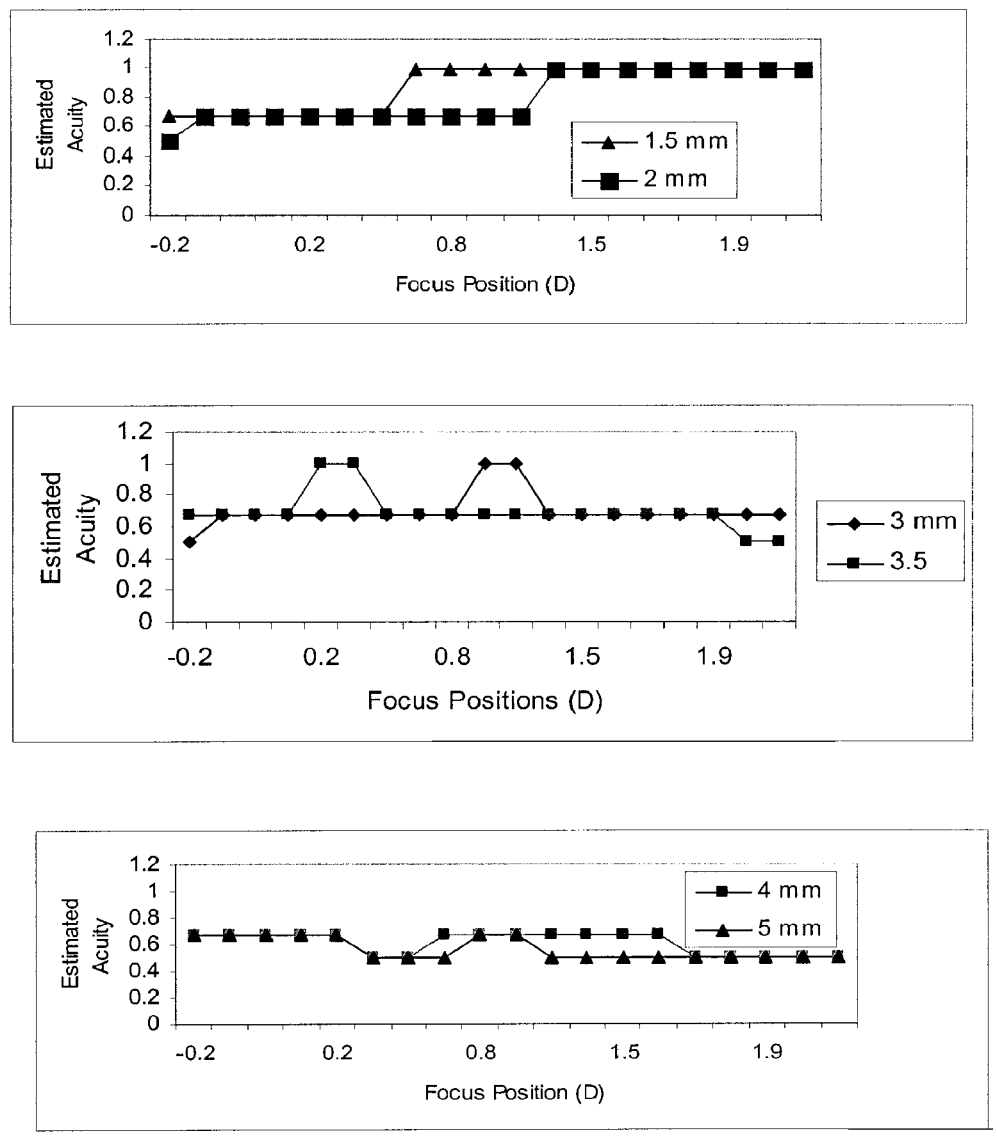
FIG. 12 shows estimated acuity of an eye with an optical element for presbyopia treatment at 5 different pupil sizes in one example for increasing focus depth of an eye by inducing spherical aberration in central pupil and controlling high-order aberrations at pupil periphery.

FIG. 11a shows the calculated modulation transfer function of an eye for a far object (0 D, top) and a near object (1.9 D, bottom) if the eye has a refractive correction according to the parameters in Table 2. Three pupil sizes are considered: 2 mm pupil on the left, 3.5 mm pupil in the middle, and 5 mm pupil on the right. The abscissa of MTF plots is spatial frequency in cycles/deg. FIG. 11b shows the calculated retinal images of acuity charts on a retina of an eye for a far object (0 D, top) and a near object (1.9 D, bottom). FIG. 12 shows estimated acuity of an eye with an optical element for presbyopia treatment at 5 different pupil sizes in one embodiment listed in Table 2.

It is seen that the estimated acuity is 20/30 or better for all pupil size less than 3.5 mm in diameter, and for far vision when the pupil size is large (4 mm or 5 mm). For a near object, the estimated acuity is 20/40 or better when pupil size is large (4 mm or 5 mm).

In another method for presbyopic corrections, significant negative spherical aberration is induced in the pupil center while spherical aberration for a large pupil in an individual eye is eliminated.

TABLE 3

Parameters of a refractive correction for presbyopia

|  | Central Pupil | Pupil Periphery |
| --- | --- | --- |
| Outer Diameter (mm) | 2.8 | 6 |
| Desired Spherical aberration $\rho^4$ (μm) | −4 | 0 |
| Focus Offset (D) | 0 | 0 |

As another example, Table 3 lists parameters for one of these corrections. First, optics of an eye is divided into two sections: the central 2.8 mm pupil and the outer pupil about 6 mm in diameter. Second, a negative spherical aberration of about −4 μm (−0.3 (Z12(r)+3.87 Z4(r)) will be induced in the central pupil while spherical aberration at pupil periphery (>2.8 mm) of an eye is mostly reduced or eliminated. The focus offset is identical for the pupil center and the pupil periphery.

Figure 13:
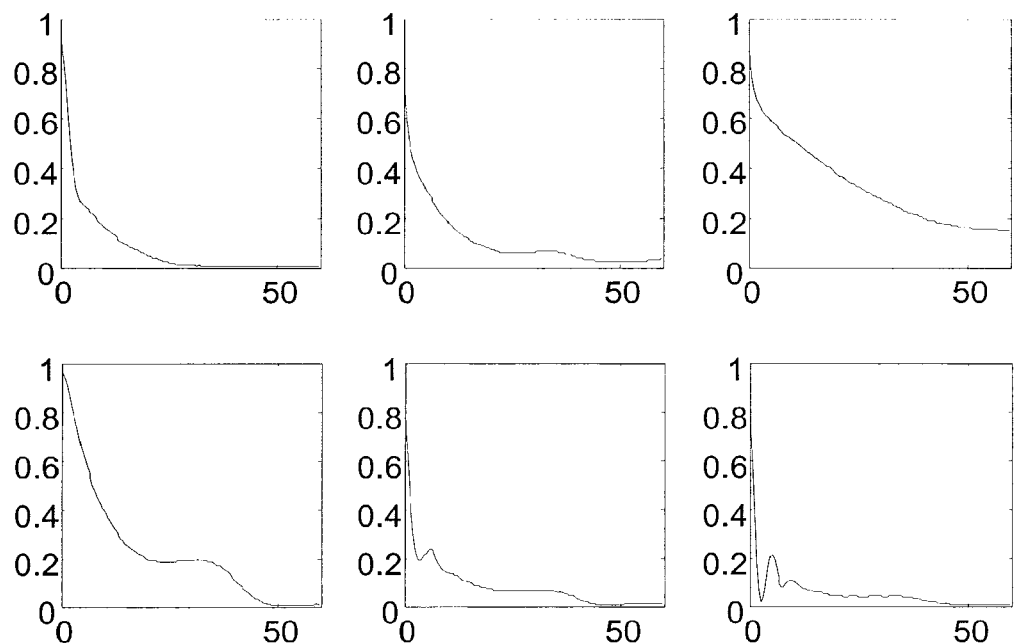
FIG. 13a shows MTFs of an eye for a far object and a near object in one embodiment for increasing focus depth of an eye by inducing spherical aberration in central pupil and controlling high-order aberrations at pupil periphery.
FIG. 13b shows calculated retinal images of acuity charts on a retina of an eye for a far object and a near object in one embodiment for increasing focus depth of an eye by inducing spherical aberration in central pupil and controlling high-order aberrations at pupil periphery.
Figure 13B:
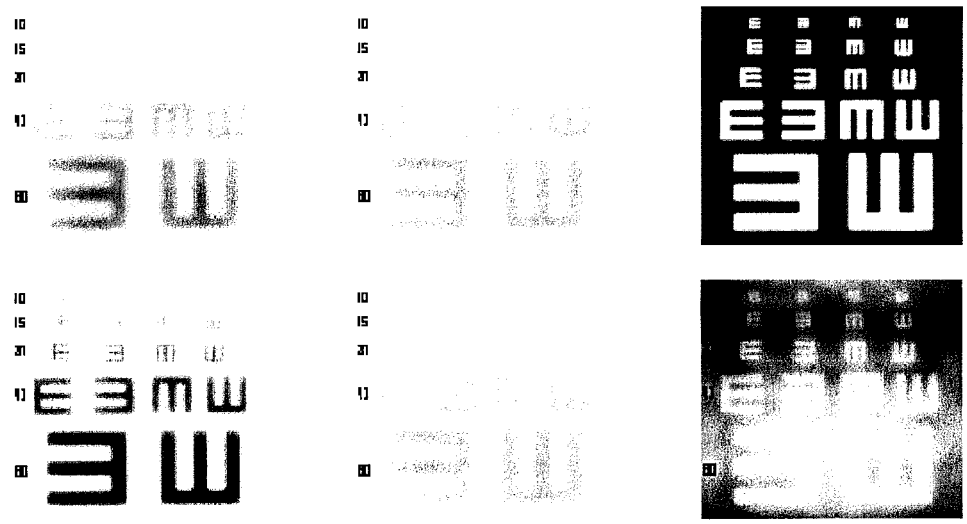

FIG. 13a shows the calculated modulation transfer function of an eye for a far object (0 D, top) and a near object (1.9 D, bottom) if the eye has a refractive distribution according to the parameters in Table 3. Three pupil sizes are considered: 2 mm pupil on the left, 4 mm pupil in the middle, and 6 mm pupil on the right. The abscissa of MTF is spatial frequency in cycles/deg. FIG. 13b shows the calculated retinal images of acuity charts on a retina of an eye for a far object (0 D, top) and a near object (1.9 D, bottom).

Figure 14:
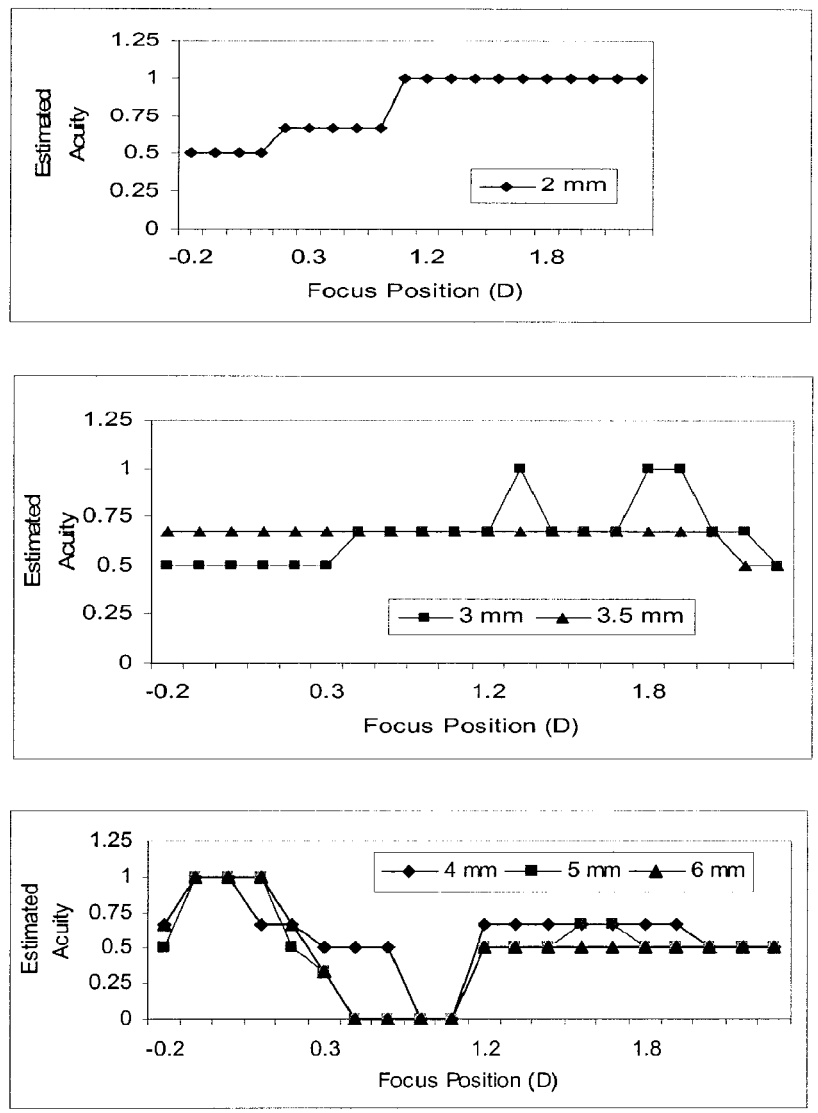
FIG. 14 shows estimated acuity of an eye with an optical element for presbyopia treatment at 6 different pupil sizes in one embodiment for increasing focus depth of an eye by inducing spherical aberration in central pupil and controlling high-order aberrations at pupil periphery.

FIG. 14 shows estimated acuity of an eye in a presbyopia treatment at 6 different pupil sizes according to parameters in Table 3. It must be noticed that the refractive correction can provide excellent acuity (20/30 or better) for far vision (around 0 D) for pupil size larger than 4 mm (at night), and for near vision (around 1.8 D) for pupil size less than 4 mm. It is also seen that the refractive correct can provide acceptable acuity (20/40 or better) for a focus depth of 2 Dioptors for pupil sizes equal to or less than 3.5 mm. It is further noticed that the refractive correction has the characteristics of a bifocal correction for pupil size larger than 3.5 mm and there is a low-acuity zone between 0.3 D and 1.2 D.

In yet another embodiment for presbyopic corrections, significant positive spherical aberration is induced in the pupil center while spherical aberration for a large pupil of an eye is corrected.

TABLE 4

Parameters of a refractive correction for presbyopia

|  | Central Pupil | Pupil Periphery |
|---|---|---|
| Outer Diameter (mm) | 4 | 6 |
| Desired Spherical aberration $\rho^4$ (μm) | 13.4 | 0 |
| Focus Offset (D) | 1.7 | 0 |

As another example, Table 4 lists parameters for one of these corrections. First, optics of an eye is divided into two sections: the central 4 mm pupil and the outer annular pupil area. Second, a positive spherical aberration of about 13.4 μm (1.0 (Z12(r)+3.87 Z4(r)) will be induced in the central pupil while spherical aberration at pupil periphery (>4 mm) of an eye is corrected. The focus offset for each optical section is 1.7 D Dioptors and 0 Dioptors, respectively.

Figure 15:
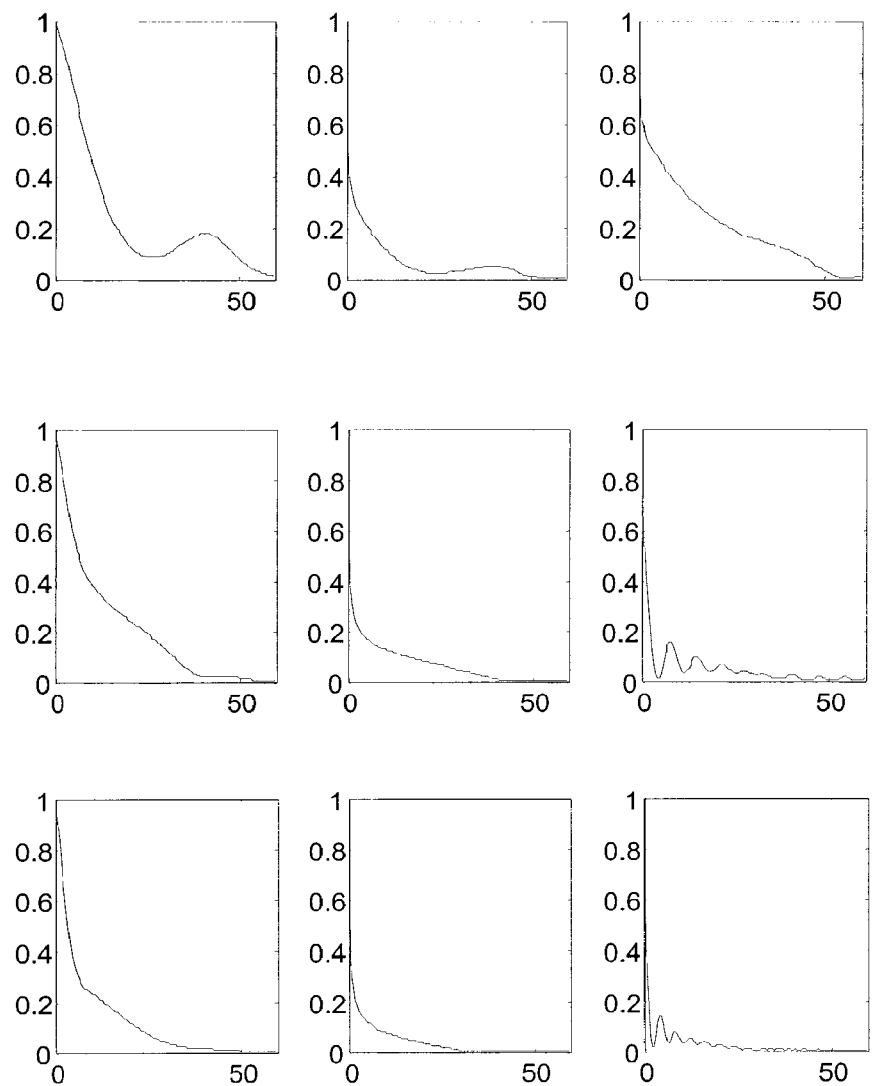
FIG. 15 shows MTFs of an eye for a far, intermediate, and near object in yet another embodiment for increasing focus depth of an eye by inducing spherical aberration in central pupil and controlling high-order aberrations at pupil periphery.

FIG. 15 shows the calculated modulation transfer function of an eye for far vision (0 D, top) and for intermediate vision (1.0 D, middle) and near vision (1.8 D, bottom) if the eye has a refractive distribution according to the parameters in Table 4. Three pupil sizes are considered: 2 mm pupil on the left, 4 mm pupil in the middle, and 6 mm pupil on the right. The abscissa of MTF plots is spatial frequency in cycles/deg.

Figure 16:
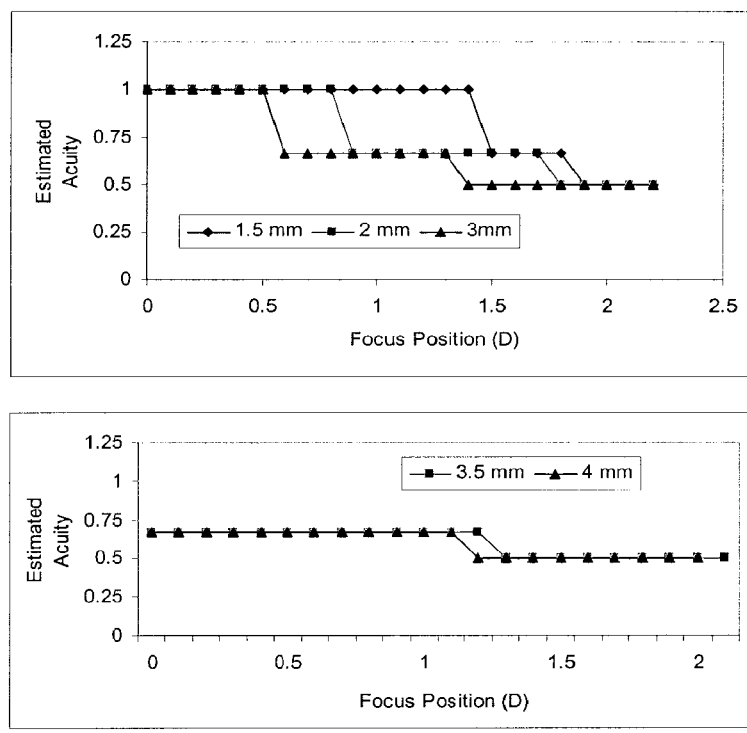
FIG. 16 shows estimated acuity of an eye with an optical element for presbyopia treatment at 5 different pupil sizes in yet another embodiment for increasing focus depth of an eye by inducing spherical aberration in central pupil and controlling high-order aberrations at pupil periphery.

It is obvious from the MTF data that the refractive correction can provide excellent far vision for night and degraded near vision at large pupil sizes. The refractive correction can provide acceptable vision (acuity of 20/40 or better) for a focus depth of 2 Dioptors for pupil sizes equal to or less than 4 mm as shown in FIG. 16.

Three embodiments for increasing focus depth of an eye by inducing spherical aberration in central pupil and controlling high-order aberration at the pupil periphery are shown. It must be pointed out that these refractive corrections listed in Table 2 through Table 4 are most appropriate for eyes with some residual accommodation (1 to 2 Dioptors). In addition to the focus offsets and spherical aberration, the refractive correction may include a conventional sphero-cylindrical correction for far vision (sphere, cylinder, and angle).

Figure 17A:
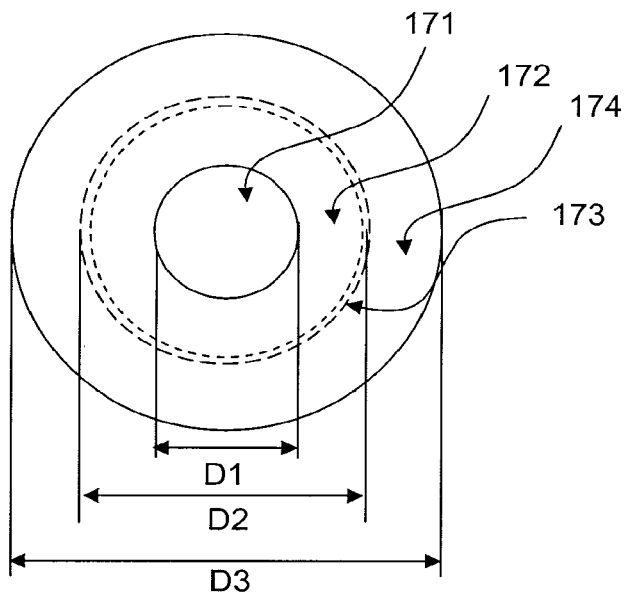
FIG. 17a shows a schematic view of an optical element for presbyopic correction that comprises two sections with controlled spherical aberration. The outer third section may or may not contain spherical aberration.

FIG. 17a shows an optical element for a presbyopic correction that comprises two sections 171 and 172 within which spherical aberration (or even high-order aberrations) is controlled. Beyond the pupil of an eye 173 for photopic vision, the outer section 173 may or may not contain spherical aberration. The diameter of the central section (D1) is between 1.8 mm and 4 mm. The diameter of the middle section (D2) is between 4 mm and 6 mm. The diameter of the outer section (D3) ranges from 6 mm to 25 mm depending on an individual implementation that includes spectacles, contact lenses, implanted contact lenses, laser refractive surgeries, and even intraocular lenses.

Figure 17B:
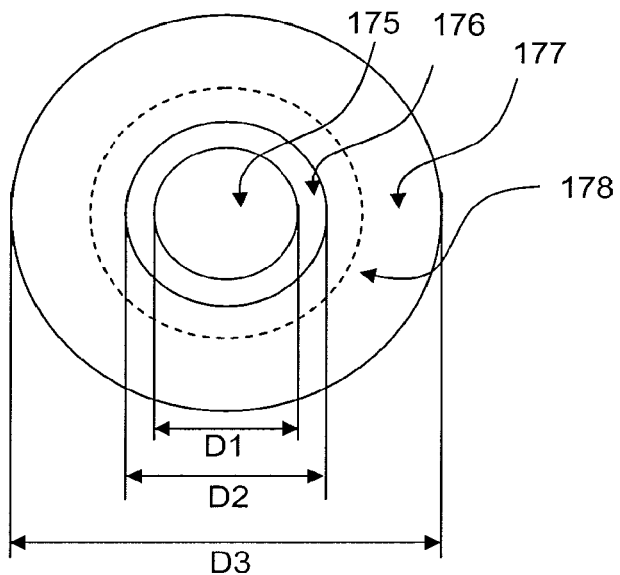
FIG. 17b shows an embodiment of a color contact lens for presbyopia treatments.

FIG. 17b shows an embodiment of a color contact lens for presbyopia treatments. It comprises of two sections 175 and 176 within which spherical aberration (or even high-order aberrations) is controlled. Beyond the middle clear section 176, the device has an annular mask blocking or attenuating light in to the eye. The diameter of the central section (D1) is between 1.8 mm and 3.5 mm. The outer diameter of the middle section (D2) is between 3.5 mm to 5 mm in diameter. The outer diameter of the outer section (D3) ranges from 8 mm to 12 mm. The optical element can be made with conventional process known in the prior art. The annular opaque or partially transparent section can be obtained by coating or tinting a portion of a clear lens section, and can also be obtained by sandwiching an opaque layer into a clear lens.

Increasing Focus Depth of an Eye by Inducing High-Order Aberrations in Central Pupil of an Eye The methods in Table 2 through Table 4 involve in precise control of spherical aberration at pupil periphery, which could be difficult for some procedures or devices. An improved method without altering high order aberration at pupil periphery would be advantageous.

Figure 18:
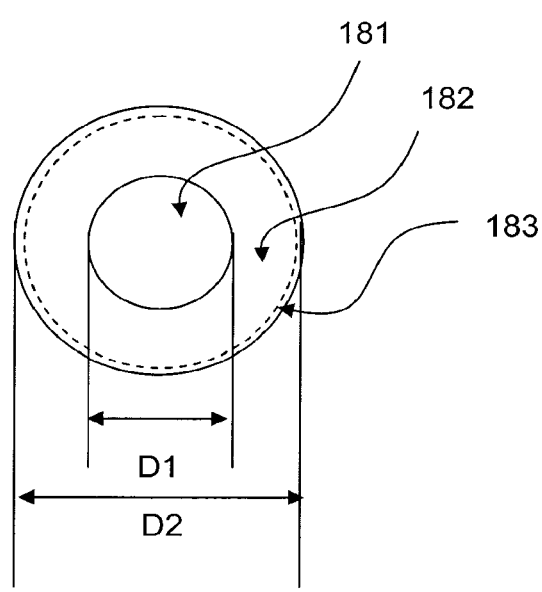
FIG. 18 shows a method for increasing focus depth of an eye by inducing spherical aberration in central pupil and without changing high-order aberrations in pupil periphery.

We describe methods for increasing focus depth of an eye for presbyopia treatments by dividing a pupil of an eye in a plurality of sections and controlling spherical aberration in the central pupil section only. As shown in FIG. 18, optics of an eye in photopic conditions is divided into two sections 181 (pupil center) and 182 (pupil periphery). We will induce spherical aberration in the central pupil 182 only but will not alter spherical aberration of an eye at pupil periphery. The diameter of pupil center 181 is between 2 mm and 4 mm and the outer diameter of D2 is between 4 mm and 6 mm. The natural pupil of an eye at mesopic condition is shown by 183.

Figure 19:
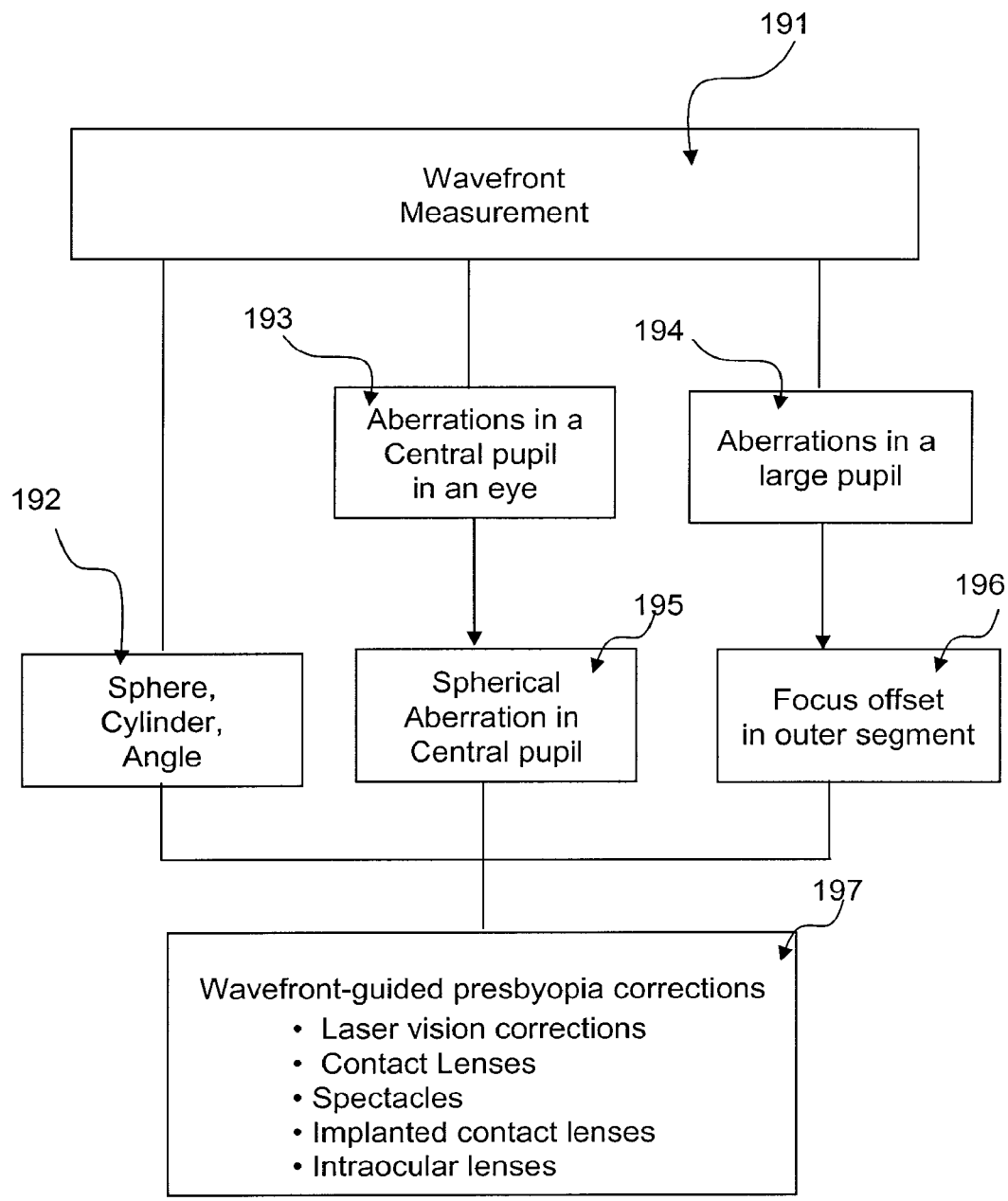
FIG. 19 shows a process for increasing focus depth of an eye by inducing spherical aberration in central pupil and without changing high-order aberrations in pupil periphery. A focus offset in the outer section is often needed, depending on high order aberration of an individual eye.

FIG. 19 shows a process for increasing focus depth of an eye by inducing spherical aberration in central pupil. First, wave aberration across pupil of an eye 191 is measured with a wavefront aberrometer. The wavefront aberrometer reports not only a conventional sphero-cylindrical correction but also high-order aberrations such as spherical aberration, coma and etc. A manifest refraction of sphero-cylindrical power as well as an accommodation range of an eye is also measured subjectively. Second, a sphero-cylindrical correction 192 for a correction element, with which the eye is made emmetropic for far vision, is determined. Third, a desired amount of spherical aberration for the central pupil (less than 4 mm) is determined. Induced spherical aberration in the eye's central pupil 195 is determined based on the desired spherical aberration and the spherical aberration 193 already in an individual eye. Fifth, a focus offsets at pupil periphery 196 is determined based on high-order aberration (spherical aberration) in an individual eye 194. Lastly, wavefront-guided presbyopic corrections 197 can be achieved for laser vision corrections, contact lenses, spectacles, implanted contact lenses and intraocular lenses based on the refractive three sets of parameters. They include a conventional sphero-cylindrical correction across entire pupil of an eye 192, magnitudes of spherical aberration in pupil center 195, and focus offsets in the pupil center and in the pupil periphery 196.

TABLE 5

Parameters of a refractive correction for presbyopia

|  | Central Pupil | Pupil Periphery |
|---|---|---|
| Outer Diameter (mm) | 2.8 | 6 |
| Desired Spherical aberration $\rho^4$ (μm) | −4 | −4 (from an eye) |
| Focus Offset (D) - Method #1 | 0 | 0 |
| Focus Offset (D) - Method #2 | 0 | −0.6 (custom determined based on high-order aberration in an eye) |

In one method, the refractive correction induces negative spherical aberration in the central pupil section but without changing high-order aberration in pupil periphery. If an eye has spherical aberration at pupil periphery, optical quality of the eye at pupil size larger than the central pupil will be determined by the spherical aberration in the eye.

As an example, Table 5 lists a hypothetical eye with known spherical aberration of −4 mm for a 6 mm pupil (−0.3 (Z12(r)+3.87 Z4(r)). The refractive correction is made to induces a negative spherical aberration of −4 mm (−0.3 (Z12(r)+3.87

Z4(r)) in the central 2.8 mm pupil while high-order aberration at pupil periphery is determined by the high-order aberrations in the eye.

Because of the spherical aberration in the eye at pupil periphery, optical quality of the eye at pupil size larger than the central 2.8 mm pupil will be different from the refractive correction listed in Table 3.

Figure 20A:
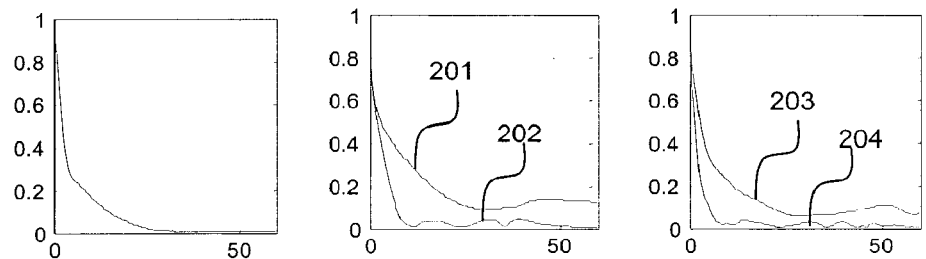
FIG. 20a shows MTFs of an eye under a refractive correction that induces significant negative spherical aberration in central pupil in two embodiments: with or without focus offset at pupil periphery. The eye is known to have a negative spherical aberration of 4 µm for a 6 mm pupil.

FIG. 20a shows the calculated MTFs of an eye under a refractive correction that induces significant negative spherical aberration in central pupil in an embodiment that has a focus offset (201 and 203) and has not a focus offset (202 and 204) between the pupil center and the pupil periphery. The eye is known to have a negative spherical aberration of 4 µm for a 6 mm pupil. Three pupil sizes are considered: 2 mm pupil on the left, 4 mm pupil in the middle, and 6 mm pupil on the right. Only MTFs for far vision are shown. The abscissa of MTF plots is spatial frequency in cycles/deg.

Figure 20B:
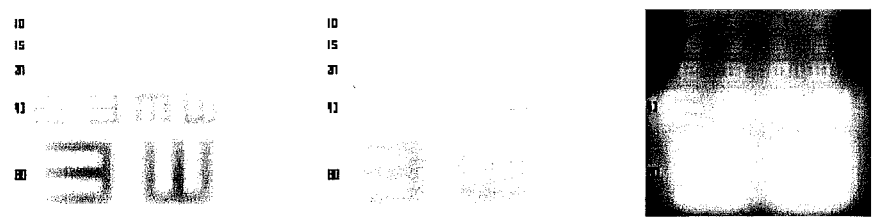
FIG. 20b shows retinal images of acuity charts in an eye under a refractive correction that induces significant negative spherical aberration in central pupil. Except for the induced spherical aberration in central pupil, the optical element has a sphero-cylindrical correction across the entire pupil of the eye.

FIG. 20b shows retinal images of acuity charts in an eye under a refractive correction that induces significant negative spherical aberration in central pupil. Except for the induced spherical aberration in central pupil, the optical element has the same sphero-cylindrical correction across the entire pupil of the eye. Three pupil sizes are considered: 2 mm pupil on the left, 4 mm pupil in the middle, and 6 mm pupil on the right. As predicted by the low MTFs 202 and 204 in FIG. 20a, retinal images of the acuity charts at a 4 mm pupil (middle) and at a 6 mm pupil (left) are severely blurred.

Figure 20C:
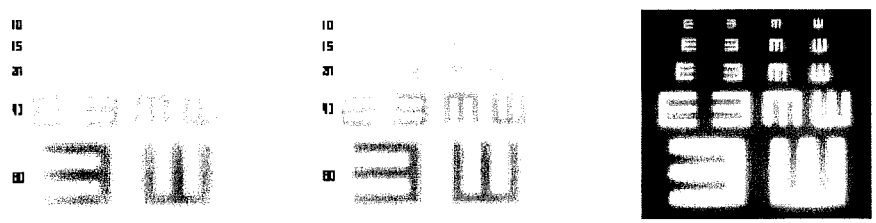
FIG. 20c shows retinal images of acuity charts in an eye under a refractive correction that induces significant spherical aberration in central pupil. In addition to the induced spherical aberration in central pupil and a sphero-cylindrical correction across the entire pupil, the optical element has a focus offset in the pupil periphery that is custom determined based on high-order aberrations in an eye.

FIG. 20c shows retinal images of acuity charts in an eye under a refractive correction that induces significant spherical aberration in central pupil in the other embodiment. In addition to the induced spherical aberration in central pupil and a sphero-cylindrical correction across the entire pupil, the optical element has a focus offset in the pupil periphery that is custom determined based on the high-order aberrations in an eye.

TABLE 6

Parameters of a refractive correction for presbyopia

| | Central Pupil | Pupil Periphery |
|---|---|---|
| Outer Diameter (mm) | 4 | 6 |
| Desired Spherical aberration ρ$^4$ (µm) | 13.4 | −4 (From an eye) |
| Focus Offset (D) - method #1 | 2 | 0 (Fixed) |
| Focus Offset (D) - method #2 | 2 | −1.25 (custom determined based on high-order aberrations in an eye) |

It is clear seen from the improved MTFs 201 and 203 in FIG. 20a lead to improved retinal images for a 4 mm pupil (middle) and for a 6 mm pupil (right), and a focus offset at pupil periphery is required to achieve acceptable image quality for medium and large pupils.

As another example, Table 6 lists a hypothetical eye with known a spherical aberration of −4 mm for a 6 mm pupil (−0.3 (Z12(r)+3.87 Z4(r)). We also assume that the refractive correction only induces a positive spherical aberration of 13.4 mm (1.0 (Z12(r)+3.87 Z4(r)) in the central 4 mm pupil while high-order aberration at pupil periphery is determined by the high-order aberrations in an eye.

Because of the spherical aberration at pupil periphery, optical quality of an eye at pupil size larger than the central pupil (4 mm) will be different from the refractive correction listed in Table 4.

Figure 21A:
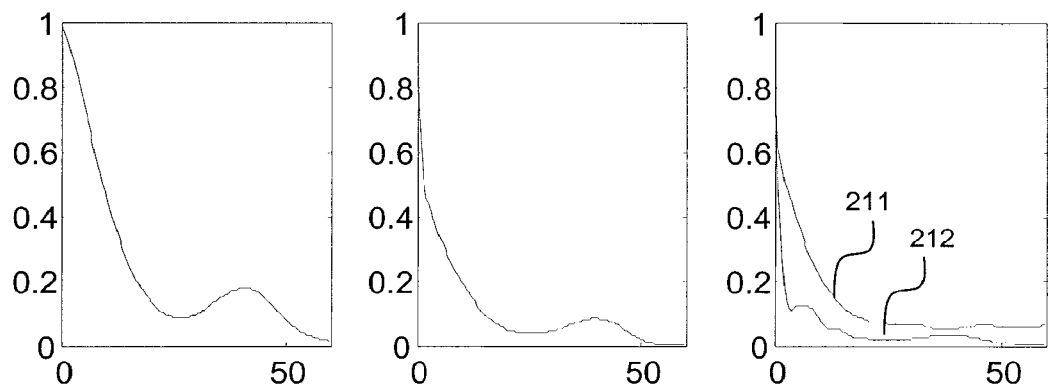
FIG. 21a shows MTFs of an eye for far vision (0D) under a refractive correction that induces significant positive spherical aberration in central pupil in two embodiments, which differ in the focus offset at pupil periphery (see Table 6).

FIG. 21a shows MTFs of an eye for far vision (0 D) under a refractive correction that induces significant positive spherical aberration in central pupil in two embodiments, which differ in the focus offset at pupil periphery (see Table 6). The eye is known to have a negative spherical aberration of 4 µm for a 6 mm pupil. Three pupil sizes are considered: 2 mm pupil on the left, 4 mm pupil in the middle, and 6 mm pupil on the right. The abscissa of MTF plots is spatial frequency in cycles/deg. For pupil sizes less than 4 mm, optical quality of the eye is identical for both embodiments as expected. However, optical quality of an eye having a refractive correction with a customized focus offset based on high-order aberrations in an individual eye 211 is significantly better than that with a fixed focus offset of 0 D.

Figure 21B:
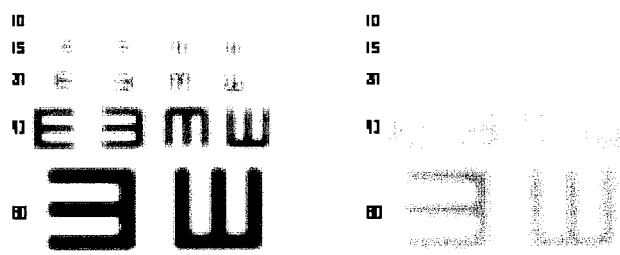
FIG. 21b shows retinal images of acuity charts in an eye under a refractive correction that induces significant positive spherical aberration in central pupil.
Figure 21B:
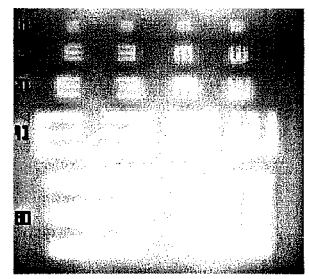
Figure 21C:
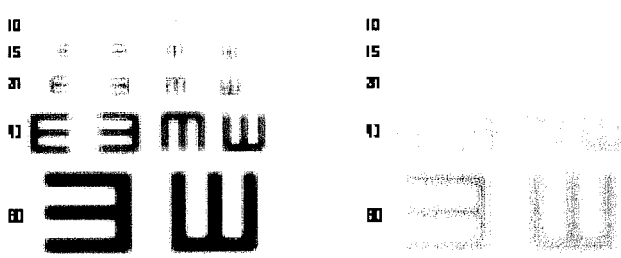
FIG. 21c shows retinal images of an acuity charts in an eye under a refractive correction that induces significant positive spherical aberration in central pupil. In addition to the induced spherical aberration in central pupil and a sphero-cylindrical correction across the entire pupil, the optical element has also a focus offset in the pupil periphery that is custom determined based on high-order aberrations in an eye.
Figure 21C:
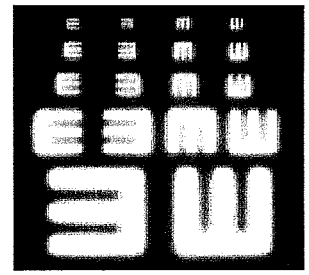

FIG. 21b shows retinal images of acuity charts in an eye under a refractive correction that induces significant positive spherical aberration in central pupil. Focus offset at pupil periphery is zero, independent of the high-order aberrations in an individual eye. Three pupil sizes are considered: 2 mm pupil on the left, 4 mm pupil in the middle, and 6 mm pupil on the right. FIG. 21c shows retinal images of acuity charts in an eye under a refractive correction that induces significant positive spherical aberration in central pupil. A focus offset at pupil periphery is determined based on the high-order aberrations in an individual eye. Three pupil sizes are considered: 2 mm pupil on the left, 4 mm pupil in the middle, and 6 mm pupil on the right. It is clear seen that a focus offset depending on the high-order aberration of an individual eye at pupil periphery can improve retinal image quality for a large pupil at night significantly.

It must be pointed out that the refractive corrections listed in Table 5 through Table 6 are most appropriate for eye with some residual accommodation (1 to 2 Dioptors). In addition to the focus offset and spherical aberration, the refractive correction may include a conventional sphero-cylindrical correction for far vision (sphere, cylinder, and angle).

Figure 22:
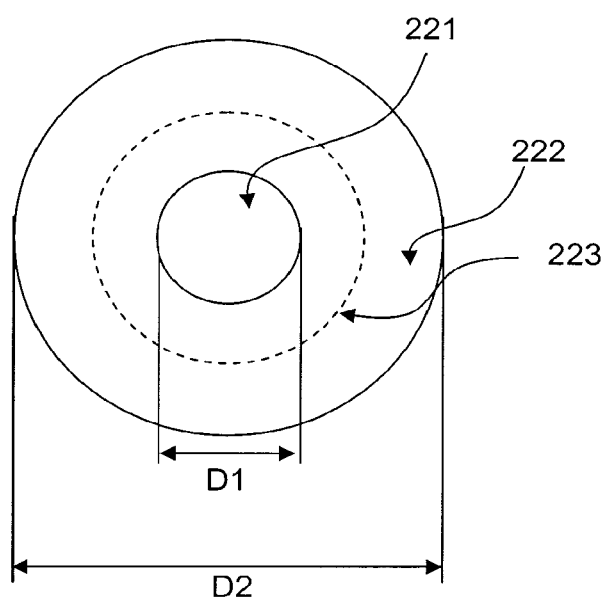
FIG. 22 shows an optical element for presbyopia treatment for an eye by inducing spherical aberration in central pupil and a custom offset of spherical power at pupil periphery based on high-order aberration in an individual eye.

FIG. 22 shows an optical element for presbyopic corrections that comprises a central sections 221 within which spherical aberration is induced for an eye at central pupil, an outer section 222 within which little or no spherical aberration (or high-order aberrations) is altered. The diameter of the central section (D1) is between 1.8 mm and 4 mm. The diameter of the outer section (D2) is 6 mm to 25 mm depending on individual implementations that may include spectacles, contact lenses, implanted contact lenses, laser refractive surgeries, and even intraocular lenses. Pupil size of an eye at a low photopic condition is shown by 222.

Figure 23:
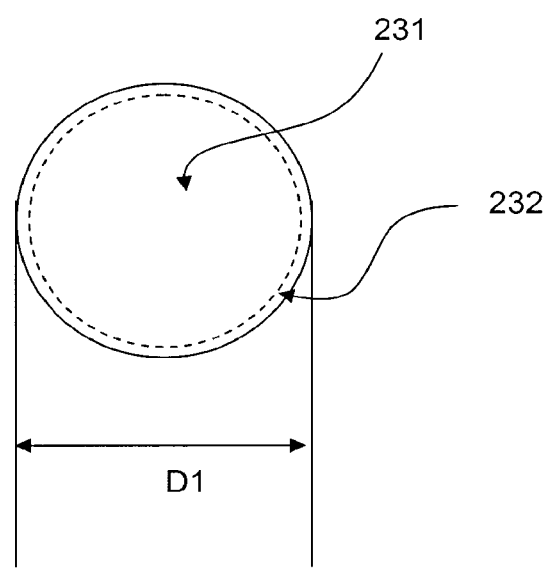
FIG. 23 shows a schematic view of a method for presbyopia treatments with induced positive spherical aberration across pupil of an eye and a focus offset to set the best image quality of an eye at the far point.

Increasing Focus Depth of an Eye by Inducing Positive Spherical Aberration Across Pupil of an Eye Increasing focus depth of an eye can also be achieved by inducing positive spherical aberration across pupil of an eye and plus a focus offset in order to set the best image quality at far vision for an eye. As shown in FIG. 23, optics of an eye under photopic conditions is shown as 231 with eye's pupil 232 for a mesopic vision condition (photopic vision at low light). The diameter of pupil (D1) is between 3 mm and 6 mm that will differ from eye to eye.

TABLE 7

Positive spherical aberration induced across pupil of an eye at mesopic conditions

| | 3 mm | 4 mm | 5 mm | 6 mm |
|---|---|---|---|---|
| spherical aberration ρ$^4$ (µm) | 4.2 | 13.4 | 32.7 | 67.8 |

Table 7 shows the total amount of positive spherical aberration induced in eyes within different pupil sizes. A focus offset (e.g., about 1.7 D) can be added to a conventional sphero-cylindrical correction in order to set the eye's best image quality for far vision of an eye.

Figure 24:
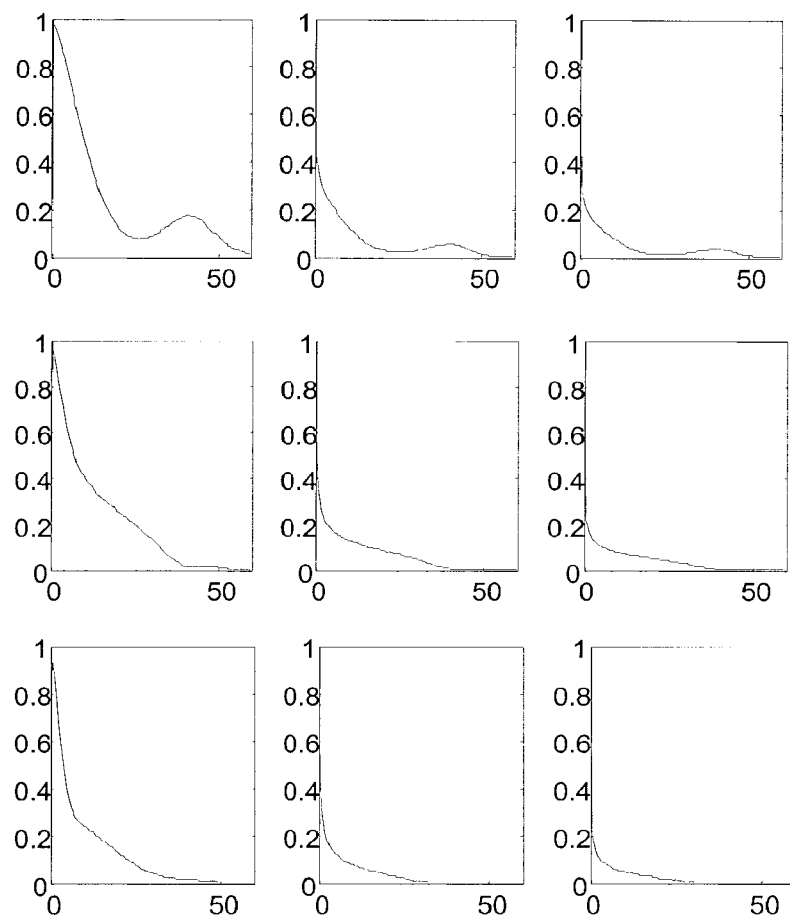
FIG. 24 shows MTF of an eye for three pupil sizes for three different object distances.

FIG. 24 shows MTFs of an eye for three pupil sizes: 2 mm on the left, 4 mm in the middle, and 6 mm on the right. Three different viewing distances are considered: 0 D (top row), 1.0 D (middle row), and 1.75 D (bottom row). Because of the huge positive spherical aberration induced by the refractive correction, high-order aberrations in a normal human eye could be ignored. The abscissa of MTF plots is spatial frequency in cycles/deg.

Figure 25:
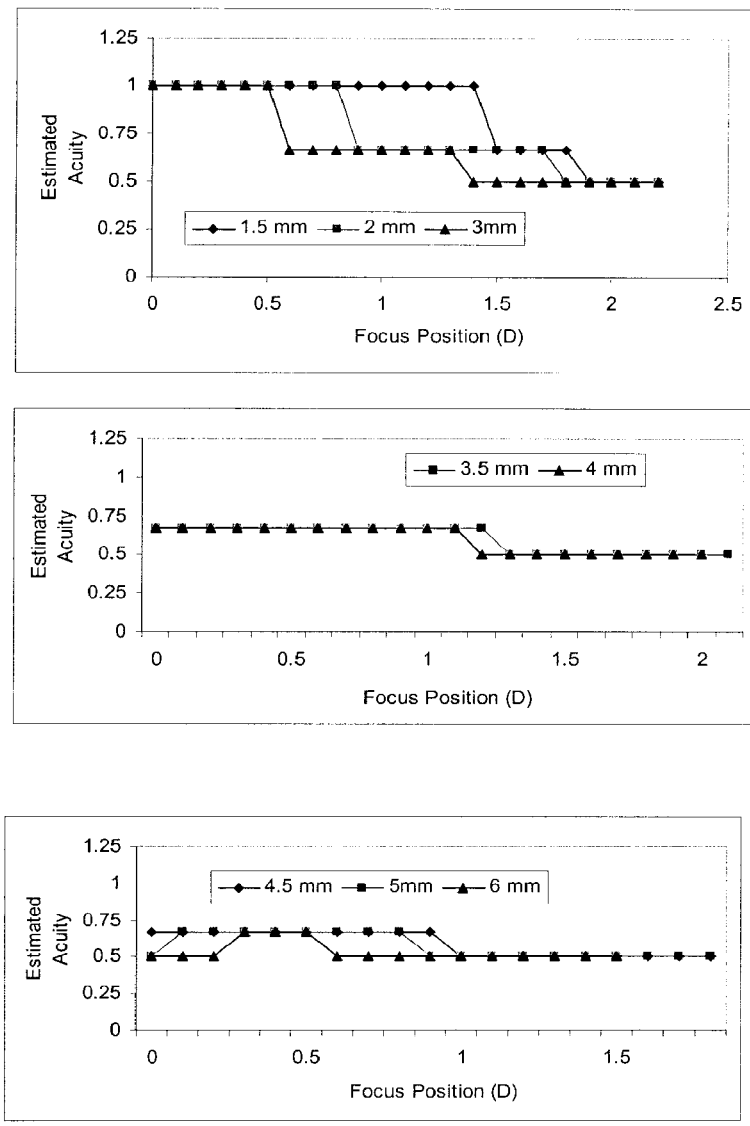
FIG. 25 shows estimated acuity of an eye with an optical element for presbyopia treatment specified in table 7.

FIG. 25 shows estimated acuity of an eye with an optical element for presbyopia treatment listed in Table 7 for 7 different pupil sizes. The refractive correction can provide acceptable vision (acuity of 20/40 or better) for a focus depth of 2 Dioptors for pupil sizes equal to or less than 6 mm in diameter. Excellent visual acuity (20/30) for far vision can be achieved for pupil size less than 4.5 mm.

Figure 26:
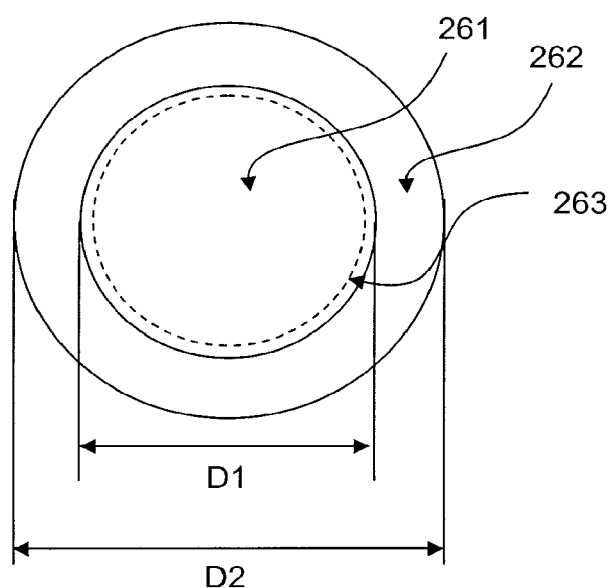
FIG. 26 shows a schematic view of an optical element for presbyopic correction that comprises a positive spherical aberration across pupil of an eye. The outer section may or may not contain spherical aberration.

FIG. 26 shows an optical element for a presbyopic correction that comprises a central optical section 261 that covers pupil of an eye 263 under photopic conditions. The diameter of the central section 261 is between 3 mm and 6 mm depending on pupil size of an individual eye. Significant positive spherical aberration will be induced across a pupil 263 of an eye at mesopic vision (photopic vision at low light). The outer section beyond the pupil of the eye 262 may or may not contain spherical aberration. The diameter of the middle section (D2) is 6 mm to 25 mm depending on individual implementations, including spectacles, contact lenses, implanted contact lenses, laser refractive surgeries, and even intraocular lenses.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the spirit and scope of the present invention. Furthermore, those of ordinary skill in the art will appreciate that the foregoing description is by way of example only, and is not intended to limit the invention. Thus, it is intended that the present subject matter covers such modifications and variations

The invention claimed is:

1. A method of treatment for presbyopia of an eye, wherein the eye has a natural pupil that comprises (a) a central pupil section at equal or less than 4 mm in diameter and (b) a surrounding periphery pupil section for receiving light at low-light conditions, the method comprising the steps of:
    inducing spherical aberration in the central pupil section; and
    preserving or reducing high-order aberrations in the periphery pupil section, the high-order aberrations being present prior to the treatment;
    wherein the spherical aberration is represented by a polynomial term and a change in refractive power of the eye occurs at an interface between the central pupil section and the periphery pupil section.

2. The method of claim 1, further comprising the step of attenuating or blocking passage of light into the eye in a periphery zone of the central pupil section.

3. The method of claim 1, wherein the spherical aberration in the central pupil section is a positive spherical aberration or a negative spherical aberration.

4. The method of claim 1, wherein the central pupil section is further divided into two concentric optical sections having spherical aberrations of opposite signs.

5. The method of claim 1, wherein the spherical aberration in the central pupil section is determined based on the natural pupil size of the eye under at least one luminance condition.

6. The method of claim 1, further comprising the step of reducing or eliminating at least one of a focus error and astigmatism in the eye.

7. The method of claim 1, wherein the reducing high-order aberrations in the periphery pupil section comprises the step of reducing or eliminating spherical aberration in the eye.

8. The method of claim 1, further comprising the steps of:
    generating an ablation pattern for laser energy for ablation of a corneal tissue of the eye, wherein the ablation pattern is based at least in part on a determined refraction profile across the natural pupil; and
    directing laser energy onto the corneal tissue of the eye to achieve the ablation pattern.

9. A method of treatment for presbyopia of an eye, wherein the eye has a natural pupil including, (a) a central pupil section at equal or less than 4 mm in diameter and (b) a surrounding periphery pupil section for receiving light during low-light conditions, the method comprising the steps of:
    producing a first set of focus power and spherical aberration in the central pupil section, to induce spherical aberration in the central pupil section; and
    producing a second set of focus power and spherical aberration in the periphery pupil section;
    wherein the first and second sets of focus power and spherical aberration create a change in refractive power at the interface between the central pupil section and the periphery pupil section.

10. The method of claim 9, wherein the spherical aberration in the central pupil section is selected to increase focus depth of the eye when the natural pupil size is equal or less than 4 mm in diameter; and wherein the focus power and spherical aberration in the pupil periphery section are selected to improve image quality for far vision during the low-light conditions.

11. The method of claim 9, wherein the induced spherical aberration in the central pupil section is determined based on the natural pupil size of the eye under at least one luminance condition.

12. The method of claim 9, wherein at least one of a focus error and astigmatism in the eye are reduced or eliminated.

13. The method of claim 9, wherein 3rd order Zernike aberrations in the eye are reduced or eliminated.

14. The method of claim 9, further comprising the steps of:
    generating an ablation pattern for laser energy for ablation of a corneal tissue of the eye, wherein the ablation pattern is based at least in part on a determined refraction profile across the pupil; and
    directing laser energy onto the corneal tissue of the eye to achieve the ablation pattern.

* * * * *